United States Patent [19]
Hercend et al.

[11] Patent Number: 5,773,578
[45] Date of Patent: Jun. 30, 1998

[54] PROTEINS PRODUCED BY HUMAN LYMPHOCYTES, DNA SEQUENCE ENCODING THESE PROTEINS AND THEIR PHARMACEUTICAL AND BIOLOGICAL USE

[75] Inventors: Thierry Hercend, Maisons Alfort; Frédéric Triebel, Neuilly, both of France

[73] Assignees: Institut National de la Sante Et de la Recherche Medicale, Paris Cedex; Institut Gustave Roussy, Villejuif Cedex, both of France

[21] Appl. No.: 416,478

[22] Filed: Apr. 4, 1995

Related U.S. Application Data

[63] Continuation of Ser. No. 854,644, filed as PCT/ER91/0009 Jan. 8, 1991, published as WO91/10682 Jul. 25, 1991, abandoned.

[30] Foreign Application Priority Data

Jan. 8, 1990 [FR] France ................................. 90 00 126

[51] Int. Cl.⁶ ........................ C07K 14/47; C07K 14/705
[52] U.S. Cl. .......................................... 530/350; 530/868
[58] Field of Search ............................ 424/185.1, 192.1, 424/810; 530/324, 350, 868

[56] References Cited

U.S. PATENT DOCUMENTS 5,109,123  4/1992  Reinharz et al. .................... 435/172.3

FOREIGN PATENT DOCUMENTS 0 329 363  2/1989  European Pat. Off. .
0 320 806  6/1989  European Pat. Off. .

OTHER PUBLICATIONS

Triebel et al. J. Exp. Med. 171:1393–1405 May 1990.
Bowie et al Science 247:1306–1310 Mar. 1990.
Chang, N.T. et al., *Chemical Abstracts* 102:181–182,216258n (1985).
Jongstra, J. et al., *J. Exp. Med.* 165:601–614 (1987).
Staunton, D.E. et al., *The EMBO Journal* 6(12):3695–3701 (1987).
Daar, E. S. et al. American Journal of Medicine 90 (4A): 22S–26S, Apr. 10, 1991.
Amzel, L.M. and Poljak, R.J., "Three–Dimensional Structure of Immunoglobulins", *Ann. Rev. Biochem.* 48:961–997 (1979).
Aviv, H. et al., "Purification of Biologically Active Globin Messenger RNA by Chromatography on Oligothymidylic acid–Cellulose", *Proc. Natl. Acad. Sci. USA* 69(6):1408–1412 (Jun. 1972).
Bowie et al., "Deciphering the Message in Protein Sequences: Tolerance to Amino Acid Substitutions", *Science* 247:1306–1310 (Mar. 1990).
Byrn, R.A. et al., "Biological properties of a CD4 immunoadhesin", *Nature* 344:667–670 (Apr. 12, 1990).
Dariavach P. et al., "Human immunoglobulin Cλ6 encodes the Kern ⁺Oz⁻λ chain and $C_\lambda 4$ and $C_\lambda 5$ are pseudogenes", *Proc. Natl. Acad. Sci. USA* 84:9074–9078 (Dec. 1987).

Davis, M. M. et al., "Cell–type–specific cDNA probes and the murine I region: The localization and orientation of $A_\alpha^d$" *Proc. Natl. Acad. Sci. USA* 81:2194–2198 (Apr. 1984).
Dayhoff, M.O. et al., "Establishing Homologies in Protein Sequences", *Methods Enzymol.* 91:524–45 (1983).
Feinberg, A.P. et al., "A Technique for Radiolabeling DNA Restriction Endonuclease Fragments to High Specific Activity", *Anal. Biochem.* 132:6–13 (1983).
Goding, "Production of Monoclonal Antibodies", Chapter 3 in: Goding, Academic Press, *Monoclonal Antibodies: Principles and Practices*:59–103 (1986).
Goding, "Purification, Fragmentation and Isotopic Labelling of Monoclonal Antibodies", Chapter 4 in: Goding, Academic Press, *Monoclonal Antibodies: Principles and Practices*:104–141 (1986).
Goding, "Generation of Conventional Antibodies", Chapter 8 in: Goding, Academic Press, *Monoclonal Antibodies: Principles and Practices*:281–293 (1986).
Gubler, U. and Hoffman, B.J., "A simple and very efficient method for generating cDNA libraries", *Gene.* 25:263–269 (1983).
Hart, C.E. et al., "Human Chromosome 12 is Required for Elevated HIV–1 Expression in Human–Haster Hybrid Cells", *Science* 246:488–491 (Oct. 27, 1989).
Huynh, T.V. et al., "Constructing and Screening cDNA Libraries in λgt10 and λgt11" D. Glover (ed), IRL Press. Oxford, UK, *DNA cloning: A practical approach*:49–78.
Kirszbaum, L. et al., "The α–Chain of Murine CD8 Lacks an Invariant Ig–Like Disulfide Bond but Contains a Unique Intrachain Loop Instead", *J. Immunol.* 142(11) :3931–3936 (Jun. 1, 1989).
Lesk, A.M. and Chothia, C., "Evolution of Proteins Formed by β–Sheets", *J. Mol. Biol.* 160:325–342 (1982).
Luckow, V.A. et al., "Trends in the Development of Baculovirus Expression Vectors", *Bio/Technology* 6:47–55 (Jan. 1988).
Maddon, P.J. et al., "Structure and Expression of the Human and Mouse T4 Genes", *Proc. Natl. Acad. Sci. USA* 84:9155–9159 (1987).
Marlin, S.D. et al., "A soluble form of intercellular adhesion molecule–1 inhibits rhinovirus infection", *Nature* 344:70–72 (Mar. 1, 1990).
Mechler, B. et al., "Membrane–bound Ribosomes of Myeloma Cells IV. mRNA Complexity of Free and Membrane–bound Polysomes", *J. Cell. Biol.* 88:29–36 (Jan. 1981).
Moingeon, P. et al., "A unique T–cell receptor complex expressed on human fetal lymphocytes displaying natural–killer–like activity", *Nature* 323:638–640 (Oct. 16, 1986).

(List continued on next page.)

*Primary Examiner*—Frank C. Eisenschenk
*Assistant Examiner*—Evelyn Rabin
*Attorney, Agent, or Firm*—Browdy and Neimark

[57] ABSTRACT

Proteins produced by human lymphocytes are described, particularly a protein which is expressed on their surface. DNA sequences coding these proteins and their pharmaceutical and biological uses are also described.

2 Claims, 9 Drawing Sheets

OTHER PUBLICATIONS

Nowill, A. et al., "Natural Killer Clones Derived From Fetal (25 wk) Blood", *J. Exp. Med.* 163:1601–1606 (Jun. 1986).

Ratner, L. et al., "Complete nucleotide sequence of the AIDS virus, HTLV–III", *Nature* 313:277–284 (Jan. 24, 1985).

Ruoslahti, E. et al., "Arg–Gly–Asp: A Versatile Cell Recognition Signal", *Cell* 44:517–518 (Feb. 28, 1986).

Ryu, S.–E. et al., "Crystal structure of an HIV–binding recombinant fragment of human CD4", *Nature* 348:419–426 (Nov. 29, 1990).

Sanger, F. et al., "DNA sequencing with chain–terminating inhibitors", *Proc. Natl. Acad. Sci. USA* 74(12):5463–7 (Dec. 1977).

Santoni, M.J. et al., "Differential exon usage involving an unusual splicing mechanism generates at least eight types of NCAM cDNA in mouse brain", *EMBO J.* 8(2):385–382 (1989).

Seed, B., "An LFA–3–cDNA encodes a phospholipid linked membrane protein homologous to its receptor CD2", *Nature* 329:840–842 (Oct. 29, 1987).

Staunton, D. E. et al., "The Arrangement of the Immunoglobulin–like Domains of ICAM–1 and the Binding Sites for LFA–1", *Cell* 61:243–254 (Apr. 20, 1990).

Triebel, F. et al., "Cloned human CD3⁻lymphocytes with natural killer–like activity do not express nor rearrange T cell receptor gamma genes", *Eur. J. Immunol.* 17:1209–1212 (1987).

Waldman, T. A. et al., "Monoclonal Antibodies in Diagnosis and Therapy", *Science* 252:1657–1662 (Jun. 21, 1991).

Wang, J. et al., "Atomic structure of a fragment of human CD4 containing two immunoglobulin–like domains", *Nature* 348:411–418 (Nov. 29, 1990).

Wegner, C. D. et al., "Intercellular Adhesion Molecule–1 (ICAM–1) in the Pathogenesis of Asthma", *Science* 247:456–459 (Jan. 26, 1990).

Williams, A.F., "A year in the life of the immunoglobulin superfamily", *Immunol. Today* 8(10):298–303 (1987).

Williams, A.F. et al., "The Immunoglobulin Superfamily—Domains for Cell Surface Recognition", *Ann. Rev. Immunol.* 6:381–405 (1988).

Yourno, J. et al., "Nucleotide Sequence Analysis of the env Gene of a New Zairian Isolate of HIV–1", *AIDS Res. Hum. Retroviruses* 4(3):165–173 (1988).

Ythier, A. et al., "Generation of Monoclonal Antibodies Blocking Cytotoxic Reactions by Human NK Clones: Further Characterization of a 40/80–kDa Target Cell Receptor", *Cell Immunol.* 99:150–159 (1986).

FIG. 5

```
        ...D....    ..E....            ...F...       ....G....              ...A...
 91   RVQLDERGRQRGDFSLWLRPARRADAGEYRAAVHLRDRALSCRLRLRL-GQASMTASPPG
276   GPDLLVTG-DNGDFTLRLEDVSQAQAGTYTCHIHLQEQQLNATVTLAIITVTPKSFGSPG
        .*   *  . ***.*.*  .*.** *.   .**... *.  . *  .   ..  ..**

..    ...B...          ...C...         ....D....      ...E....       ..
150   SLRASDWVILNCSFSRPDRPASVHWFRNRGQGRVPVRESPHHHLAESFLFLPQVSPMDSG
335   SL------GKLLCEVTPVSGQERFVW--------SSLDTPSQRSFSGPWL-EAQEAQLLSQ
      ,**       * * .       *    *       ..  ... .. .*  *. . . *

..F.....        ....G...
210   PWGCILTYRDGFNVSIM-YNLTVLGLEP..
381   PWQCQL-YQGERLLGAAVY-FTELSS-PGA
      ** * *..    ..  * .* *    *
```

FIG. 6

```
                      L         ↓        ..A..      ...B....
LAG-3  MWEAQFLGLLFLQPLWVAPVKPLQPGAEVPVVWAQEGAPAQLPCSPTIPLQDLSLLRR-A
CD4    MCRGFSFRHL-LPLLLLQLSKLLVVTQGKTVVLGKEGGSAELPCESTS--------RRSA
       *  .  *   *  .   ↑*  *     **  .**..*.***  .*          ** *

..C...   ↓                        ....C'...  ..C"..
  32   GVTWQHQPDSGPPAAAPGHPLAPGPHPAAPSSWGPRPRRYTVLSVGPGGLRSGRLPLQPR
  25   SFAWKSSDQ-----------------------------KTILGYKNKLLIKGSLELYSR
       . .*.    .                           *.*.     * * * * .*
                                                            ↑
       ..D....   ...E...         ...F...      .....G....  ↓...A...
  92   VQLDERGRQRGDFSLWLRPARRADAGEYRAAVHLRDRALSCR-LRLRLGQASMTASPPGS
  55   FDSRKNAWERGSFPLIINKLRMEDSQTYVCELENKKEEVELWVFR------VTFNPGTR
       .    ...** *.* .    * *. *   ..  .   . .*     .* .*
                                                            ↑
       .     ....B..       ...C...        ....D....    ...E....    .
 151   LRASDWVILNCSFSRPDRPASVHWFRNRGQGRVPVRESPHHHLAESFLFLPQVSPM--DS
 108   LLQGQSLTLILD-SNPKVSDPPIECKHKSSNIV---------KDSKAFSTH-SLRIQDS
       *   .. .*    * *  . *   ...  *       .*  *  . *    **

....F....        ...G...↓     ...A...    ...B....        ...
 209   GPWGCILTYRDGFNVSIMYNLTVLGLEPP-TPLTVYAGAGSRVGLPCRLPAGVGTRSFLT
 156   GIWNCTVTLNQKKHSFDM-KLSVLGFASTSITAYKSEGESAEFSFPLNL--GEES-LQGE
       * * *  .*    .    * .*.***. .         *  . ..* * .   .
                              ↑
       .C..                              ....D..    .....E....    ....
 268   AKWTPPG--------------------GGPDLLVTGDNGDFTLRLEDVSQAQAGTYT
 212   LRWKAEKAPSSQSWITFSLKNQKVSVQKSTSNPKFQLS-ETLPLTLQIPQVSLQFAGSGN
       .* .                             .*  . . .  .**.. .**  **.

F.....    ....G....  ↓   ....A..   ...B....     .....C...
 305   CHIHLQEQQLNATVTLAIITVTPKSFGSPGSLGKLLCEV-TPVSGQERFVWSSLDTRSQR
 371   LTLTLDRGILYQEVNLVVMKVTQ-----PDS-NTLTCEVMGPTSPKMRLILKQENQEARV
        . *.     * *  *   **        .*   * *** *    *   . *..    . ..
                             ↑
       ....E.....     ...F....    ...G...     ↓
 364   SFSGPWLEAQEAQLLSQPWQCQLYQGERLLGAAVYFTELSSPGAQRSGRAPGALPAGHLL
 325   SRQEKVIQVQAPE--AGVWQCLLSEGEEVKMDSKIQV-LSKGLNQ-----------TMF
       *      ..  *..    .* ***  .**  .     .  ↑ **      *       .

___TM_____  .    ↓
 424   LFLTLGVL-SLLLLVTGAFGFHLWRRQWRPRRFSALEQGIHPRRLRAR..........
 370   LAVVLGSAFSFLVF-TGLCILFCVRCRHQQRQAARMSQIK--RLLSEKKTCQCSHRMQKS
       * . **  *.*.. **   *    * .* . .* *     * * . *
                                            ↑
       ....
 427   HNLI
```

Immunoprecipitation of membrane proteins of PHA-blasts well No. 1 : preimmune hetero-antiserum well No. 2 : hetero-antiserum well No. 3 : non-immunoprecipitant Mab well No. 4 : anti-CD2 Mab "Western blot" detection of LAG-3S using a hetero-antiserum in the baculovirus system:

well No. 1 : LAG-3S supernatant well No. 2 : LAG-3S supernatant well No. 3 : AcNPV supernatant well No. 4 : LAG-3S supernatant revealed by a preimmune hetero-antiserum;

PROTEINS PRODUCED BY HUMAN LYMPHOCYTES, DNA SEQUENCE ENCODING THESE PROTEINS AND THEIR PHARMACEUTICAL AND BIOLOGICAL USE

This application is a continuation of application Ser. No. 07/854,644 filed Sep. 8, 1992, now abandoned, which was based on international application PCT/FR91/00009 filed Jan. 8, 1991, published as WO91/10682 Jul. 25, 1991, now abandoned.

BACKGROUND OF THE INVENTION

1. Field of the Invention

The present invention relates to proteins produced by human lymphocytes and, in particular, to a protein expressed at the surface of the latter, DNA sequences coding for these proteins and the pharmaceutical and biological uses of these proteins.

2. Description of the Related Art

A certain number of protein structures of the cell surface "belong" to the "superfamily" of the immunoglobulins (IgSF). This family of molecules includes the proteins comprising at least one domain with a characteristic folding region called the Ig fold. Several of these molecules have essential functions in immune responses.

In addition to ensuring specific antigen recognition, as do for example the immunoglobulins and the T receptors, they may function as monomorphic ligands critical in cell-cell interactions (for example ICAM, CD4, CD8), receptors for viruses (for example CD4, ICAM) or receptors for the lymphokines (for example IL1-R, IL6-R).

The discovery and characterization of the membrane proteins expressed on the lymphocytes have been facilitated by the development of genetic engineering techniques. By means of various experimental techniques, this methodology makes it possible to characterize the genes coding for the proteins and hence to deduce the peptide sequence from knowledge of the nucleotide sequence of the gene. Other applications of these genetic engineering techniques based on the same experimental principles enable virtually unlimited quantities of the proteins corresponding to the genes which have been discovered to be produced as a consequence of procaryotic or eucaryotic systems of expression.

SUMMARY OF THE INVENTION

The inventors have attempted to discover novel genes coding for hitherto undescribed membrane proteins.

The development of the experiments of the inventors has led to the isolation of a novel complementary cDNA designated FDC from natural cytotoxic lymphocytes. This cDNA codes for a protein called LAG-3 (for Lymphocyte Activation Gene-3) which possesses a signal sequence which is thought to be removed to generate the mature protein.

Consequently, the present invention relates to a DNA sequence comprising the nucleotide sequence designated FDC, corresponding to the cDNA sequence represented in the sequence SEQ ID No. 1.

Translation starts at nucleotide 231 and ends at nucleotide 1724.

The present invention also relates to the protein encoded by FDC, namely the protein LAG-3 represented in the sequence ID NO:9 (protein sequence renumbered 1 to 498).

The first 28 amino acids should constitute a signal sequence which has been removed in the mature protein.

Hence, the present invention relates more particularly to the protein corresponding to the protein sequence 1 to 470 of SEQ ID NO.7.

The mature protein constitutes a membrane protein of type I of 470 amino acids, the theoretical molecular mass of which deduced from the protein structure is 51295 daltons and the isoelectric point is 10.9. It comprises an extracellular region containing about 420 amino acids and a cytoplasmic region containing about 24 amino acids linked by a transmembrane peptide containing about 26 amino acids. The extra-cellular part of the LAG-3 protein corresponds to the amino acids 1 to 420 of the LAG-3 protein described above.

Comparison of the sequence of the LAG-3 gene represented by the cDNA FDC above as well as the exon/intron organisation of the LAG-3 gene with those of other molecules of the Ig/SF type has revealed a close relationship of the LAG-3 protein with the CD4 protein.

It is known that the genes of eucaryotic cells exhibit the phenomenon of polytypy. As a result of this phenomenon, some of the amino acids of the coded protein are sometimes replaced without modification of the activity. The present invention includes the proteins resulting from this phenomenon.

Hence, the present invention relates more generally to a protein having the peptide sequence corresponding to the sequence SEQ ID No. 2, SEQ ID NO:7, SEQ ID NO:9 and the sequences which differ from it by one or more amino acids and which possess the same activity.

Furthermore, the inventors have found a DNA sequence which is a promoter region for a gene coding for a protein according to the invention. This sequence is that represented in sequence SEQ ID No. 4.

Consequently, the present invention also relates to this DNA sequence.

The present invention also relates to a DNA sequence comprising the promoter DNA sequence as defined above and a DNA sequence coding for a protein according to the present invention.

In the present invention, the inventors first isolated an FDC complementary DNA by means of the following operations.

- culture of lymphocyte cells known as natural cytotoxic cells
- isolation from these lymphocytes of the messenger RNA bound to the membranes of the intracellular endoplasmic reticulum
- isolation of the single-stranded complementary DNA from the messenger RNA, then of the double-stranded complementary DNA
- insertion in a vector such as the bacteriophage lambda gt10
- preparation of a single-stranded DNA probe from the messenger RNA of the cells and purification by means of a subtraction-hybridization technique so as to select the copies of the RNAs present in the natural cytotoxic lymphocyte cells and absent from other transformed hematopoietic cells.
- selection of the complementary DNAs inserted into the vector which react with the probe
- transfer of the DNA selected into a plasmid vector in order to amplify, purify and sequence it.

The protein sequence according to the invention was obtained by:

translation of the nucleotide sequence of the FDC cDNA.

The existence of this protein in the natural state on T cells was demonstrated by:

preparation of sera directed against a synthetic peptide representing a region probably exposed toward the exterior of the product of translation of the FDC cDNA which has a protein structure in the form of a loop, immunoprecipitation of the LAG-3 protein by anti-peptide hetero-antibodies.

The proteins according to the invention may also be obtained by other methods of purification of membrane proteins or by classical peptide synthesis or also by application of genetic engineering techniques comprising the insertion of a DNA sequence coding for a protein according to the invention into an expression vector such as a plasmid and the transformation of cells with this expression vector and the culture of these cells.

Hence, the present invention also relates to plasmids and expression vectors comprising a DNA sequence coding for a protein according to the invention as well as hosts transformed with this vector.

The present invention also relates to a therapeutic composition containing as active ingredient a protein according to the invention or a part of this protein, in particular the soluble part corresponding to the extracellular region of the protein extending from amino acid 1 to amino acid 420 of the protein sequence previously described or a part of this extracellular region and, in particular, all or part of at least one of the four extracellular domains of the immunoglobulin type of the LAG-3 protein (sequences 1 to 142, 143 to 232, 233 to 342 and 343 to 413). The part of the protein may also be constituted by all or part of the cytoplasmic region (sequence 450 to 470). The extracellular part may, in particular, be the sequence represented in the sequence SEQ ID No. 3.

This therapeutic composition is active in the treatment of certain diseases implicating the immune system in which the binding of the ligand(s) of the LAG-3 protein to this protein causes the transmission of signals into the interior of the cell, or modifications of cellular interactions.

In this case, the composition according to the invention may act by binding the ligand(s) of the membrane protein LAG-3, thus preventing the detrimental binding of this ligand or these ligands to the LAG-3 protein by a phenomenon of competitive inhibition.

The present invention also relates to monoclonal antibodies directed against a protein according to the invention or an immunogenic sequence of such a protein, in particular a peptide sequence comprising the sequence represented in SEQ No. 3.

The present invention also relates to hybridomas producing such monoclonal antibodies.

The present invention also includes the fragments and derivatives of the monoclonal antibodies according to the invention which react with defined regions of the LAG-3 protein. Such fragments are, in particular, the F(ab')$_2$ fragments which may be obtained by enzymatic cleavage of the antibody molecules with pepsin, the Fab' fragments which may be obtained by reduction of the disulfide bridges of the F(ab')$_2$ fragments and the Fab fragments which may be obtained by enzymatic cleavage of the antibody molecules with papain in the presence of a reducing agent. These fragments as well as Fv fragments may also be obtained by genetic engineering.

The monoclonal antibody derivatives are, for example, antibodies or fragments of these antibodies to which markers such as a radioisotope are linked. The monoclonal antibody derivatives are also antibodies of fragments of these antibodies to which therapeutically active molecules, in particular cytotoxic substances, are linked.

Furthermore, the monoclonal antibodies or the soluble fractions of the LAG-3 protein and, in particular, all or part of at least one of the four extracellular domains of the immunoglobulin type of the LAG-3 protein (sequences 1 to 142, 143 to 232, 233 to 342 and 342 to 413) or the cytoplasmic region (sequences 450 to 470) of this protein may be used in the treatment of human diseases due to infection by viruses of the HIV type.

These same products may be used in the treatment of human diseases in which a pathophysiological mechanism causes intercellular adhesion interactions between a ligand and LAG-3 (in particular with the first and/or second external domain of LAG-3) such as, for example, the auto-immune diseases.

They may also be used in the treatment of the human diseases caused by viruses binding specifically to the LAG-3 molecule and, in particular, to the first, $NH_2$-terminal external domain.

The present invention also relates to a dosing or identification method for the proteins according to the invention which comprises the use of the monoclonal antibodies according to the invention.

For this purpose it is possible to use, in the case in which a part of the LAG-3 protein is soluble in the native state, a radio-immunological method of the RIA type or the IRMA type (technique of the sandwich type using a cold antigen and competition between a cold antibody and a labelled antibody) or an immuno-enzymatic method of the ELISA type or the IEMA type (technique of the sandwich type).

In order to identify the LAG-3 protein bound to the membrane, it is possible to use methods such as direct immunofluorescence (using anti-LAG-3 antibodies labelled with a fluorescent substance) or indirect immunofluorescent (by using a labelled anti-Ig mouse immunoglobulin in the case in which the anti-LAG-3 antibodies have been produced in this species).

The monoclonal antibodies directed against the proteins according to the invention or fractions of them may be prepared according to a standard method. For this purpose, the protein fractions may be coupled if necessary to an immunogenic agent such as tetanus toxoid by means of a coupling agent such as glutaraldehyde.

A more detailed description will be given hereafter of the isolation of the FDC CDNA and the LAG-3 gene coding for the protein by referring to the appended Figures.

FIG. 1 presents the restriction map of the FDC cDNA and the clones of cDNA which have enabled the sequence of the FDC clone to be determined;

FIG. 2 presents the restriction map and the distribution of exons and introns in the LAG-3 gene;

FIG. 3 is a schematic representation of the LAG-3 protein;

FIG. 4 presents a model of the domain 1 of the LAG-3 protein; (corresponding to amino acid residues 1 to 139 of SEQ ID NO:7);

FIG. 5 presents the alignment of the domains 1 and 2 (corresponding to amino acid residues 304 to 264 of SEQ ID NO:9) with the domains 3 and 4 (corresponding to amino acid residues 304 to 435 of SEQ ID NO:9) of the LAG-3 protein;

FIG. 6 presents the alignment of the peptide sequences of LAG-3 (SEQ ID NO:9) and the CD4 (SEQ ID NO:8) protein of the rat;

FIG. 7 presents the result of an immunoprecipitation of membrane proteins of PHA-blasts;

FIG. 8 is a schema for the preparation of a transfer vector (baculovirus system);

FIG. 9 presents the result of the detection by immofluorescence of LAG-3C in the baculovirus system by means of a heteroantiserum;

FIG. 10 shows by immunofluorescence the reactivity of a heteroantiserum on PHA-blasts and PBL;

FIG. 11 presents the result of the detection of LAG-3S in the baculovirus system by means of a heteroantiserum in a Western blot.

DESCRIPTION OF THE PREFERRED EMBODIMENTS

Figure 1:
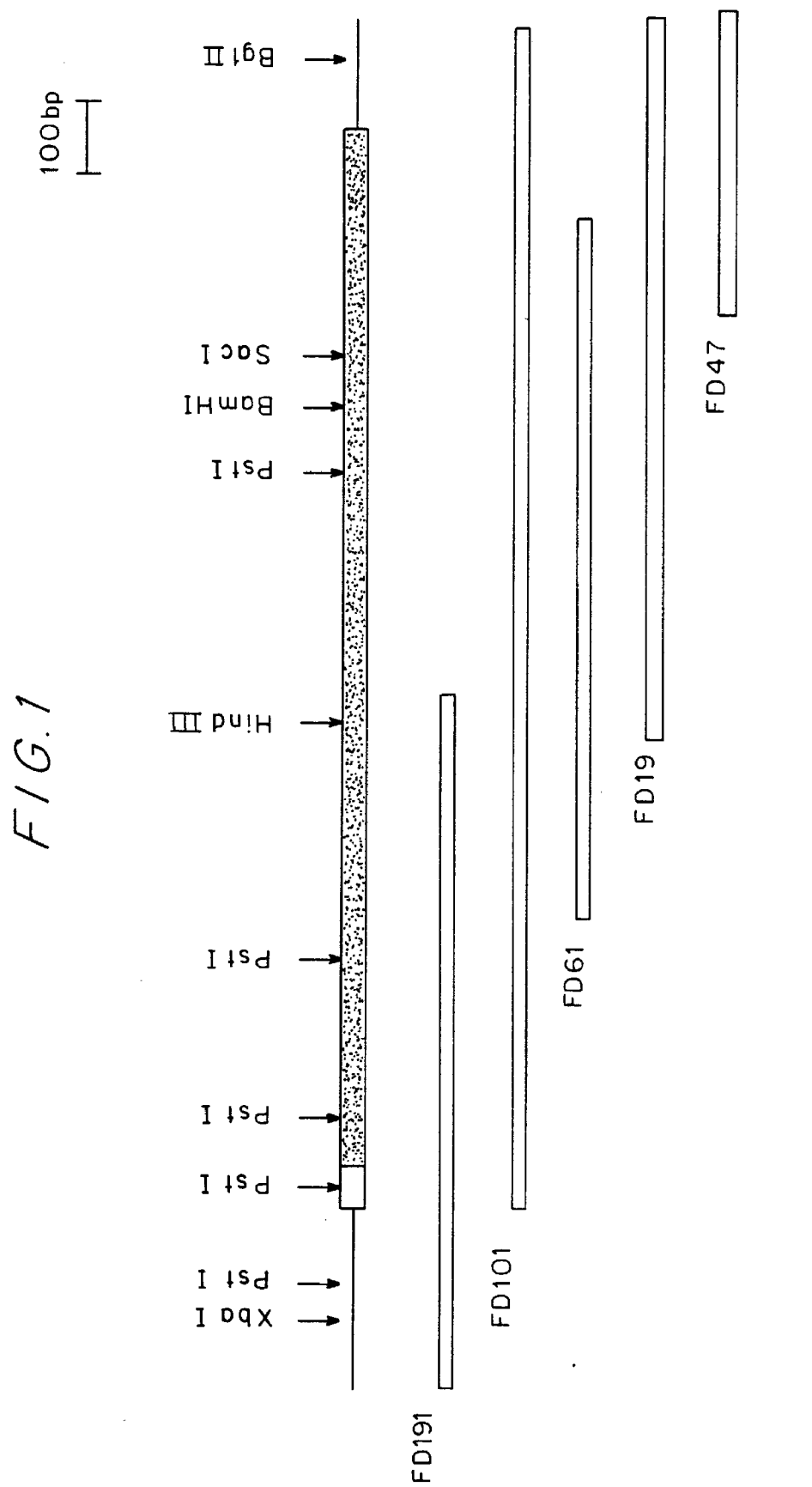

I—Culture and Preparation of the mRNA Linked to the Membranes of the Endoplasmic Reticulum The isolation and the characteristics of the fetal clone, F55IIIE5 (phenotype CD3⁻ CD2⁺) have been previously described by Nowill et al (1).

The mass culture was carried out in the presence of recombinant interleukin-2 and the supernatant of lymphocyte-conditioned medium on a feeder substratum of allogenic irradiated mononucleated blood cells and a cell line transformed by the EBV virus (called LAZ 388) on V-bottomed 96-well plates. 3000 cells were placed in each well at day 0. The pooling of 200 plates with $3 \times 10^6$ cells per ml at day 12 gave a harvest of $6 \times 10^9$ cells.

The preparation of the cytoplasmic RNAs, the RNAs bound to the membranes of the endoplasmic reticulum and the mRNAs was performed by introducing some modifications to the methods described by Maniatis (2), Mechler (3) and Aviv (4). Thus, $4 \times 10^9$ F55IIIE5 cells were loaded onto sucrose gradients after hypotonic shock and mechanical grinding according to the method described by Mechler. The cytoplasmic RNAs borne by the ribosomes bound to the membranes of the endoplasmic reticulum were purified between sucrose gradients. This makes it possible to work subsequently with mRNAs which have a signal sequence and which consequently code for proteins borne by the membrane or secreted into the internal part of the ergastoplasm (and towards the exterior of the cell). This method of isolation of RNA of the so-called MB (membrane-bound) type makes it possible to remove right away about 90% of the transcribed genes which code for intracellular proteins incapable of being secreted towards the exterior or transported towards the membrane and, consequently, of no interest in the context of the invention. In addition to the isolation of the MB-F55IIIE5 mRNA which serves as substrate for the construction of the library, on the one hand, and the preparation of the probe, on the other, the methods of purification described by Aviv (4), Maniatis (2) and Triebel (5) made possible the isolation of RNAs of the various clones and cell lines which are used and mRNAs of Jurkat, U937, Laz388 and K562 cells (about $10^9$ cells of each line) which are used to subtract the probe.

These methods comprise:

A—Preparation of the cytoplasmic RNA 1 ml of lysis buffer (50 mM Tris HCl, 62.5 mM EDTA, 0.4% Triton X-100 surfactant, 2.5M LiCl) is added to a vial containing 20 to $30 \times 10^6$ cells as a dry pellet. After gentle dissolution of the pellet, the lysis buffer is transferred to cold EPPENDORF tubes containing 50 $\mu$l of 10% NP40.

After 5 minutes on ice, the tubes are centrifuged for 1 min at 8000 rev/min. The supernatant (RNA) is removed and introduced into FALCON tubes containing 1 ml of phenol, 1 ml of CHCl₃, 1 ml of STE 2% SDS (150 mM NaCl, 10 mM Tris, 1 mM MgCl₂, 2% SDS). The tubes are centrifuged for 10 min. at 5000 rev/min. The upper phase is removed, 1 ml of phenol and 1 ml of chloroform are added. After centrifugation for 5 min. at 5000 rev/min., the upper phase is removed. 100 $\mu$l of 0.2M EDTA, 200 $\mu$l of 3M NaAc and 5 ml of ethanol are added. The mixture is left at −20° C. overnight before being centrifuged for 30 min at 10000 rev/min. The pellet is dried. It is taken up in 400 $\mu$l of cold 0.3M NaAc. 1 ml of ethanol is added to the FALCON tube. The ethanol is transferred to the EPPENDORF tube, the mixture is left for 1 h at −20° C. The mixture is centrifuged for 10 min at 13 K, the alcohol is aspirated and the pellet is dried. 30 $\mu$l of water are added. The solution is centrifuged and frozen immediately at −80° C. The degradation and the amount are checked by placing 1 $\mu$l on a denaturing gel (1% agarose in TBE buffer (Tris, Base, EDTA), pH 8.5, autoclaved (BET 1 $\mu$g/ml).

B—Preparation of the Messenger RNA Bound to the Membranes of the Endoplasmic Reticulum The cells are taken up in ice-cold hypotonic RSB buffer (10 mM KCl, 1.5 mM MgCl₂, 10 mM Tris-HCl, pH 7.4) treated beforehand with 0.1% DEPC at $10^8$ cells/ml. They are left on ice for 5 min. The cells are ruptured mechanically by means of 10 strokes of a DOUNCE homogenizer (type B). The homogenate is centrifuged at 1000 g for 2 min in order to sediment the nuclei. The supernatant or "cytoplasmic extract" is then used for the separation of free ribosomes/membrane extracts. 0.7 ml of cytoplasmic extract is mixed with 3.2 ml of 2.5M sucrose TK buffer (0.05M Tris-HCl, pH 7.4, 0.15M KCl, 0.005M MgCl₂), then this mixture is layered onto 2 ml of 2.5M sucrose TK. 8 ml of 2.05M sucrose TK are added, followed by 4 ml of 1.3M sucrose TK. The gradients are centrifuged at 4° C. for 5 h in a swinging rotor of the SPINCO SW28 type at 25000 rev/min. The tubes are punctured with a needle at the interphase between the 2.05M and the 1.3M sucrose gradients. One volume equal to TE 10:1 (10 mM Tris HCl, 1 mM EDTA) is added. An extraction is made with phenol, then with a phenol-chloroform mixture. Precipitation is effected with ¹⁄₁₀ of 3M NaAc and 2.5 vol. of ethanol.

For the isolation of the poly (A)⁺ RNA a column of oligo (dT)-cellulose is used containing 1.2 ml of gel equilibrated with the loading buffer: 20 mM Tris-HCl (pH 7.6), 0.5M NaCl, 1 mM EDTA supplemented with SDS. The column is washed with H₂O, a 0.1M NaOH solution and 5 mM EDTA and water. It is then washed with 5 volumes of loading buffer. The RNA is dissolved in water and heated at 65° C. for 5 min. An identical volume of loading buffer is added twice. The temperature is allowed to equilibrate. The effluent is collected. It is heated at 65° C. and the sequence is repeated. The column is washed with 5 to 10 volumes of loading buffer, then with 4 volumes of loading buffer-0.1M NaCl. The poly(A)⁺ is eluted with 2–3 volumes of 10 mM Tris-HCl (pH 7.5), 1 mM EDTA, 0.05% SDS. 3M sodium acetate (pH 5.2) is added at ¹⁄₁₀. Precipitation is effected with 2.2 vol. of ethanol.

II—Construction of the cDNA Library

The in vitro preparation of the single-stranded complementary DNA starting from the messenger RNA bound to the membranes of the endoplasmic reticulum of the F55IIIE5 cell, followed by the double-stranded complementary DNA is carried out according to the techniques described by Gubler et al (6).

After protection of the internal EcoRI sites by the EcoRI methylase and size selection on an agarose gel at low temperature permitting the selection of fragments of size larger than 500 bp, the double-stranded cDNAs were cloned into the EcoRI site of the phage Lambda gt10 with the aid of the EcoRI linker.

The in vitro packaging of the recombinant Lambda gt10 phages was performed using a commercial cloning kit (Amersham Corp. Arlington Heights, Ill).

After plating on E. coli C 600 Hf1+, 6×10⁴ recombinant phages are obtained.

III—Preparation of the Complementary DNA Probe

The preparation of the single-stranded complementary DNA probe is carried out by subtraction by means of two cycles of hybridization on an excess of messenger RNA of the cells said "to be eliminated" (Jurkat, Laz 388, U937, K562), followed by passage through hydroxyapatite columns which enables the double-stranded cDNA-mRNA complex to be separated. After 2 hybridization cycles and 2 passages through the column about 6–7% of the radioactivity remain, i.e. that about 7% of the F55IIIE5 material called MB ("membrane-bound") does not exist in the Jurkat, K562, U937 and Laz 388 cells. It is this material which serves as probe for the detection of the corresponding cDNAs in the MB-F55IIIE5 library. This technique makes use of the subtraction-hybridization conditions described by Davis et al (7).

Preparation of the subtracted probe/MB-FSSI-IIES-mRNA of Jurkat, K562, Laz 388, U937/

Starting from 5 µg of MB-F55IIIE5 mRNA, a single-stranded cDNA probe is prepared labelled with $^{32}$P-dCTP (specific activity: 800 Ci/mmol$^{-1}$) in a volume of 50 µl.

After incubation for 2 h at 42° C. with the reverse transcriptase enzyme, 5 µl of 0.2M EDTA are added, followed by 50 µl of 0.2N NaOH. The mixture is incubated at 65° C. for 1 h. 60 µl of 1N HCl and 30 µl of 2M Tris-HCl (pH 8) are added. ⅒th vol. of 3M NaAc is added. 7 µl of mRNA of each of the 4 tumor lines are added in order to precipitate the probe, then 2.5 vol. of ethanol are added.

The mixture is left for 1 h at −20° C. before being centrifuged, washed with 70% ethanol and dried. The precipitate is taken up in 7.5 µl of H$_2$O, and 7.5 µl of 0.5M NaH$_2$PO$_4$, pH 7, 1mM EDTA, 0.25% SDS are added. The solution is incubated in the incubator at 68° C. for 20 hours.

The solution is diluted with 1 ml of 0.12M NaH$_2$PO$_4$, 0.1% SDS. It is loaded onto a hydroxyapatite column equilibrated with the same buffer at 60° C. The effluent (single-stranded material) is concentrated using 2-butanol and passed through a G-50 column in order to remove the phosphate buffer. 7 µg of mRNA of each of the lines are added again and the hybridization and passage through the column are repeated. After these 2 passages, 7% of the starting amount of radioactivity are recovered.

IV—Isolation and Characterization of the cDNA Clones

The previously constructed cDNA library (2×10⁴ recombinant phages) is inoculated into E. coli C600/Hf1. The screening is performed in accordance with the usual techniques using nylon filters as described by Huynh (8).

Hybridization with the probe previously obtained is carried out at 42° C. with prehybridization with a hybridization solution of the Southern type and addition of 5×10⁶ cpm/ml of the single-stranded MB-F55IIIE5 subtracted probe.

After two subtraction-hybridization cycles, 120 positive lambda gt10 phages are identified out of the 2×10⁴ recombinants.

The plating of the positive phages, the purification of the corresponding DNAs, the purification of the complementary DNAs in the form of fragments by excision from an agarose electrophoresis gel with a low gelling point were carried out according to the method described by Maniatis (2) and Huynh (8).

The ligation of the longest cDNAs in the plasmid vector pBS digested by the EcoRI endonuclease and treated with the alkaline phosphatase calf intestine, the transformation of competent JM 109 bacteria and the screening of the recombinants by a double selection system (ampicillin+X-gal/IPTG) were carried out according to the methods of genetic engineering conventionally used.

The purification and the preparation on a large scale of the recombinant complementary DNAs cloned in pBS were carried out by using the method of purification on a cesium chloride gradient described by Mianiatis (2).

A cDNA clone was isolated which has been designated FD47 and which consists of 400 bp and hybridizes with the probe obtained by subtraction-hybridization. This clone was selected, on the one hand, because it hybridizes with a transcript of 2 kb constantly found in the F55IIIE5 cells but not in the Jurkat, Laz 388, K 562 and U 937 cells in the "Northern blot" techniques and, on the other, because it shows no homology with any of the known sequences of the data bank entitled "Genebank". The FD47 clone contains a nucleotide region capable of coding for a hydrophobic transmembrane region.

V—Isolation and Structure of a Full-length DNA.

Among the 120 positive lambda gt10 phages obtained after subtraction-hybridization, no other phage was observed to cross-hybridize with FD47.

In order to establish the sequence of cDNA called FDC, three new cDNA libraries are constructed starting either from oligo-dT primers, or a hexamer of random sequence or a specific primer consisting of the nucleotides 704 to 688 of FDC. Furthermore, a single-stranded RNA probe labelled with $^{32}$p is constructed starting from FD47 by in vitro transcription from the pBS plasmid using the T7 polymerase in the presence of $^{32}$P-UTP (800 Ci.mmole$^{-1}$) according to the method described by Triebel (5). The three libraries are constructed from the messenger RNA derived from CD3+ clones bearing the γ and δ of the T receptor and which transcribe a LAG-3 message in considerable quantities when their RNA is tested with the FD47 probe.

The FD47 probe is used to screen the first cDNA library in order to obtain the clone FD19.

In the same manner as previously described, a 0.3 kb Bam HI - Hind III genomic fragment comprising the most 5' part of the IV exon is labelled using as primer a random hexamer and it is used to screen the second library to obtain the clones FD61 and FD101, and the third library in order to obtain a cDNA containing the almost full-length 5' end, called FD191.

The sequences of the clones FD47 and FD19 were determined directly in the pBS vector by the method of Sanger (9) using a universal M13 primer or a reverse 113 primer and the modified T7 polymerase.

The sequences of FD61, FD101 and FD191 were determined front single-stranded DNA after cloning in the vector M13mp18.

After different overlapping cycles of hybridization ("DNA walking") by using the 3 cDNA libraries obtained using different primers, cDNA clones are thus isolated, the sequences of which overlap and which cover a total of 1.8 kb.

The set of the total nucleotide sequences of these cDNAs called "FDC sequence" consisting of 1871 bp indicates that the messenger RNA of the LAG-3 gene has a long and open reading frame and codes for a protein of 498 amino acids, the peptide sequence of which is obtained by deduction from the nucleotide sequence of the cDNA.

The FDC cDNA itself was obtained by ligation of the 2 complementary FcoRI-HindIII fragments, one covering the 5' part of the FD191 clone, the other covering the 3' part of the FD19 clone, thus producing a clone covering the entire known sequence, as illustrated in FIG. 1.

VI—Isolation and Structure of the LAG-3 Gene

A/ Molecular cloning of the LAG-3 gene

Genomic DNA clones are isolated from the LY67 library made from DNA of a human B cell line transformed by EBV, partially digested with Mbo-I and inserted into the phage lambda 2001 as described by Dariavach (10). The FD47 insertion segment is labelled by means of the hexamer random priming method described by Feinberg (11) and used to screen $2 \times 10^5$ plaques of the human genomic DNA library. Nine positive plaques (GD1 to GD9) are isolated and the phage DNAs are characterized by restriction mapping using the FD19 probe containing half of the region coding for the protein and the untranslated 3' region.

Figures 2, 3:
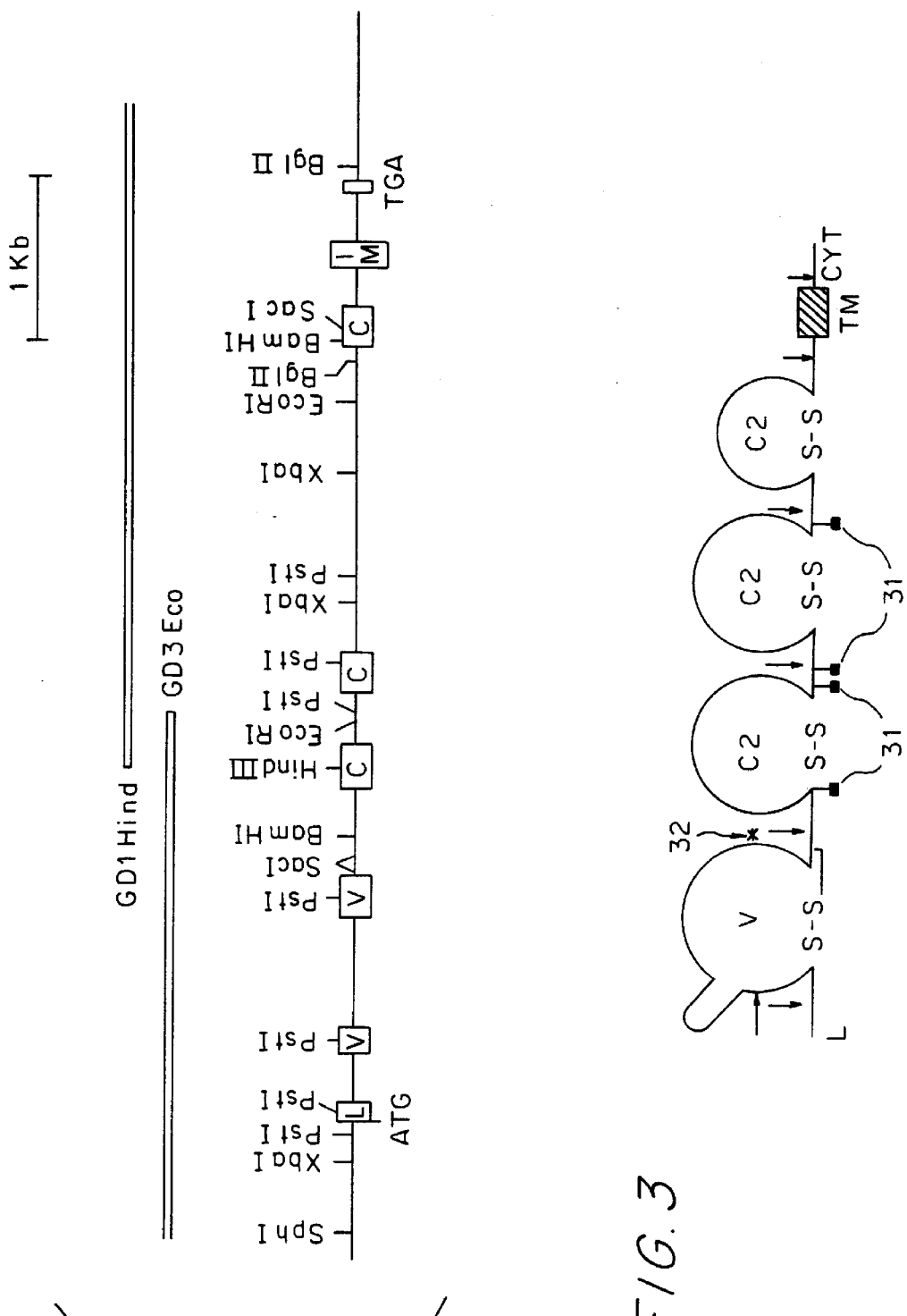

Two overlapping DNA fragments of 16.4 kb (EcoRI) and 11.5 kb (Hind III) are obtained and subcloned in the plasmid pUN121 to give the clones GD3Eco and GD1Hind, as shown in FIG. 2.

Detailed restriction maps of these subclones are constructed and compared with the restriction map of the FDC sequence shown in FIG. 1.

Many fragments are obtained on an agarose gel with a low gelling point and are subcloned in the bacteriophages M13mp18 or M13mp19.

The sequences of these fragments are determined from single-stranded DNA using the dideoxy chain termination procedure described. Oligonucleotides containing 17 bases, the sequences of which are obtained either from the cDNA of FD19 or from the sequence of the 5' flanking region of the LAG-3 gene are synthesized and used for sequencing.

B—Structure of the LAG-3 Gene

FIG. 2 illustrates the exon-intron organisation of the human LAG-3 gene. The map was constructed after single and double digestion by endonucleases of the $GD_2$ and $GD_3$ clones obtained from lambda 2001 and their subclones $GD_3$ Eco and $GD_1$ Hind. The untranslated regions are represented by a fine line.

The LAG-3 gene spans approximately 6.6 kb and is divided into 8 exons, the first nucleotides of which are located at positions 1, 289, 437, 742, 1012, 1288, 1531 and 1662 of the DNA sequence previously described.

The so-called promoter region at the 5' end of the LAG-3 gene whose sequence was previously described has been studied and enabled the following observations to be made:

no characteristic TATA box is found upstream from the 239-bp untranslated 5' region;

the nucleotide sequence contains a CCAAT box in reverse (i.e. ATTGG) at position −662 from the ATG sequence signalling the initiation of translation.

The CCAAT box is known to be crucial in many promoters and may function in the reverse orientation.

an Sp1 binding site containing the typical GGGCGG core hexanucleotide is also located at position −389 from the translation initiation site.

In order to estimate the number of copies of the LAG-3 gene in the human genome, the DNA of the K562 tumor cell line and of the polyclonal IL-2-dependent T and NK cell lines are digested with EcoRI, Hind III, Bam HI or XbaI. Southern Blot hybridizations are performed using the FDC probe (1871 bp), constructed by fusion of the 5' EcoRI/Hind III fragment of the FD191 clone with the 3' Hind III/EcoRI fragment of the FD19 clone. 3 fragments of 2, 8.2 and 10 kb are obtained with EcoRI, 2 fragments of 5.7 and 9.5 kb with Hind III, 3 fragments of 2.8, 4 and 13 kb with Bam HI and 3 fragments of 3, 4 and 6 kb with XbaI.

These results indicate that a single copy of the LAG-3 gene is present in the human haploid genome. Furthermore, the analysis of the T, B and NK cells using the same technique shows that there is no rearrangement of the LAG-3 gene in the cells during the differentiation of the lymphocytes.

VII—Expression of the LAG-3 gene

The 1004 bp fragment inserted in the FD19 clone was used as probe to analyse the cellular distribution of the expression and the regulation of the expression of the LAG-3 gene.

The results of the RNA "blotting" clearly show that the subtraction-hybridization procedures used in the first screening of the F55IIIE5 sub-library were performed successfully with respect to the isolation of the FD19 clone of the cDNA library in the sense that no LAG-3 transcript is expressed in the transformed cell lines of T, B and myeloid origin (in particular Jurkat, Laz 388, K 562, U 937).

Assays were performed on other lines of transformed T cells including CDI and MOLT-4 and none was found to express LAG-3. The same was true for the peripheral circulating monocytes.

A selection of polyclonal lines or clones of normal T and NK cells placed in culture was also tested. In the latter case, LAG-3 messenger RNA was detected as a single species of about 2 kb in all of the lines studied: 3 $CD3^-$ lines (F55 III E5, SIIH4, SIII G5), 4 $CD3^+$ TCR $/\beta^+$ lines ($CD4^+$: SIF8 and F55IIIG5 and one $CD3^+$ TCRτ/$\delta^+$ line (the clone TCRδ1$^+$ TiτA$^+$ BK).

However, messenger RNA was not detected in fresh, purified T cells nor in peripheral macrophages nor in resting lymphocytes, within the limits of detection usually accepted for this technique.

The expression of the LAG-3 gene has also been studied in the nervous tissues of neuroectodermal origin and no messenger RNA was detected in either the neuroblastoma cell lines in culture or in fresh cerebral tissue.

The LAG-3 gene is only expressed in the T and NK cells after activation.

The expression of the LAG-3 gene is maximal 3 to 4 days after activation of the blood lymphocytes by phytohemagglutinin. Hence, the protein corresponds to what is appropriately called an activation antigen.

VIII—Structure of the LAG-3 Protein

Figure 4:
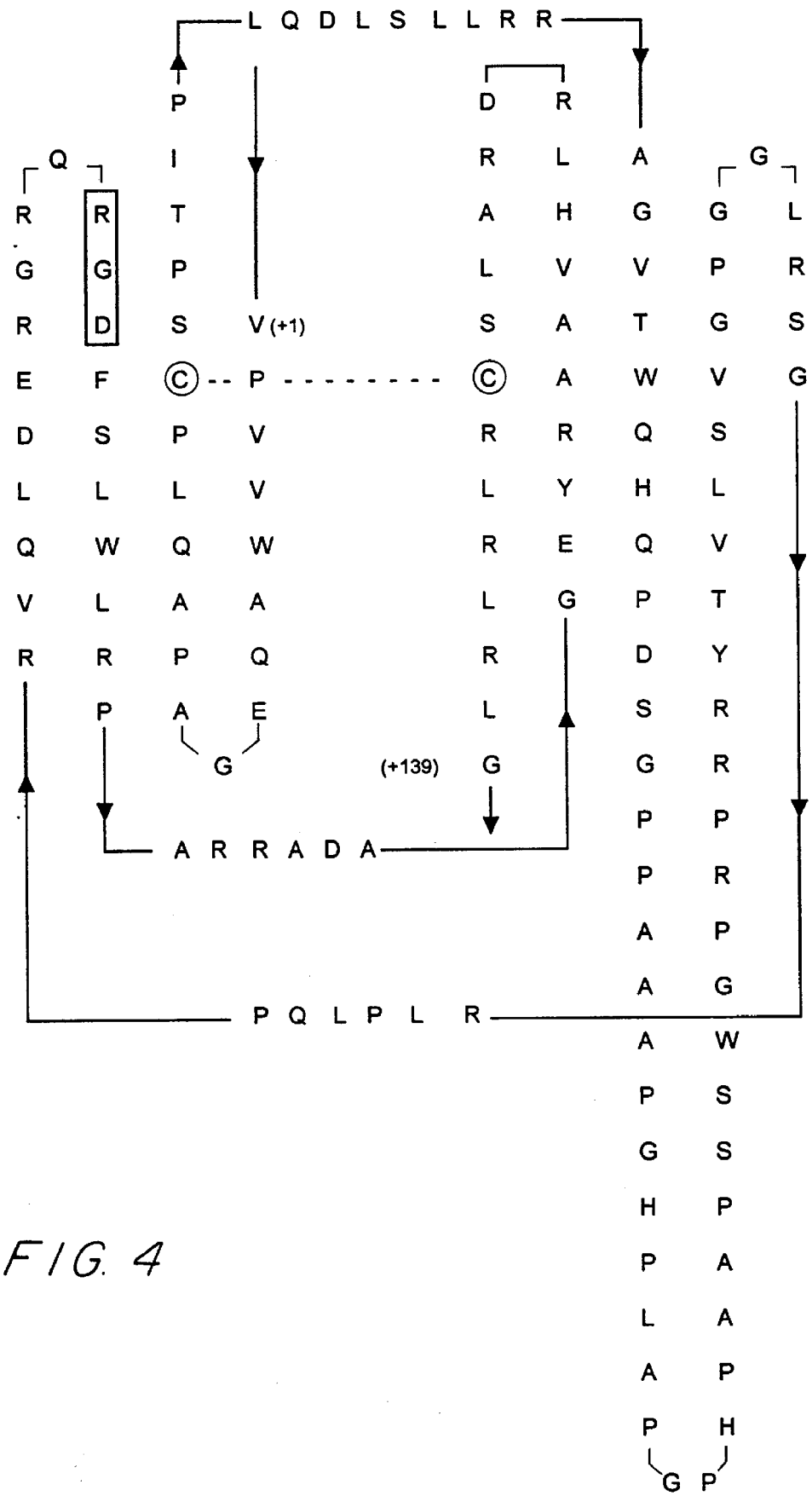
Figure 7:
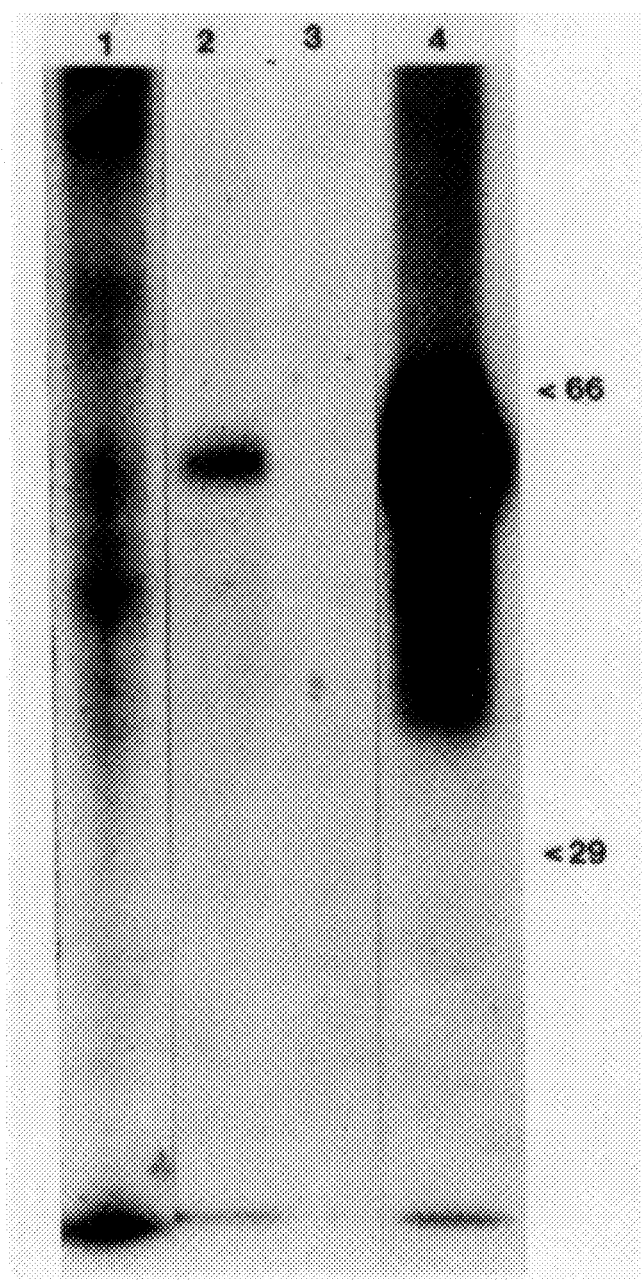
Figure 8:
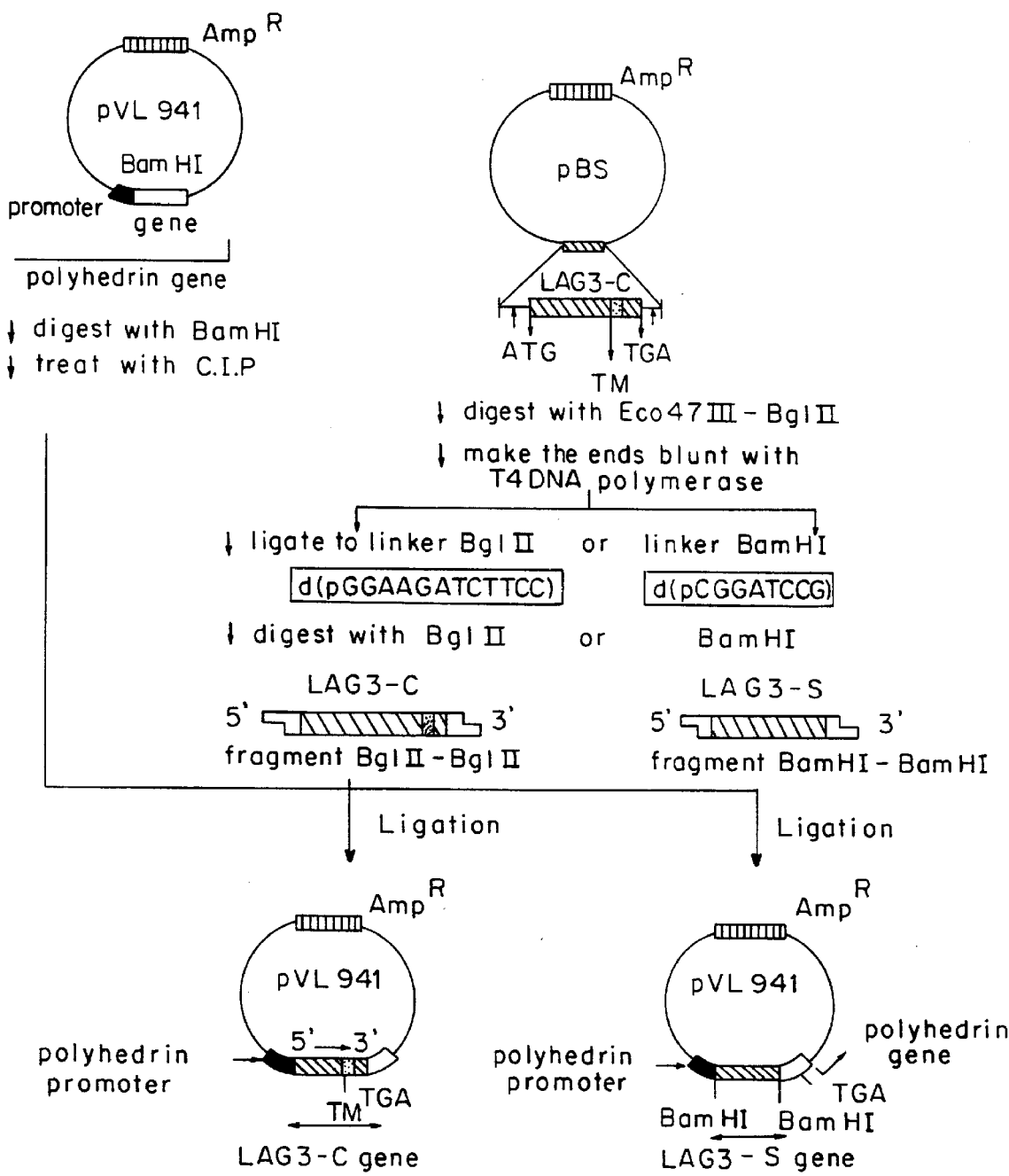

The characteristics of the LAG-3 protein, shown in FIGS. 3, 4 and 6, have been deduced from the structure of the gene and from the analysis of its translation product. It appears to be a type I membrane protein containing 498 amino acids.

As shown in FIG. 3, the domains are designated by L (leader domain), V (V domain of the immunoglobulin type), $C_2$ ($C_2$ domain of the immunoglobulin type) (19), TM (transmembrane) and CYT (cytoplasmic). The position of the introns is indicated by arrows. The N-glycosylation sites 31 and the RGD sequence 32 (cell attachment sites) are also indicated.

The mature protein comprises 470 amino acids with a theoretical molecular mass of 51295 daltons and an isoelectric point of 10.9 based on protein structure analysis. It contains a leader peptide L (28 amino acids) encoded by the exons I (19 amino acids) and II (9 amino acids out of 50). The extracellular region is encoded by the exons II (41 amino acids out of 50), III (101 amino acids), IV (90 amino acids), V (92 amino acids) and VI (81 amino acids), the transmembrane (TM) region by the exon VII (44 amino acids) and the cytoplasmic region including strongly charged amino acids by the exon VIII (21 amino acids). The extracellular region contains 8 cysteine residues and 4 potential N-glycosylation sites (Asn-X-Ser, Thr).

FIG. 4 presents a model of domain 1 of the LAG-3 protein. The sequence of the first domain of the Ig type (amino acids +1 to +139) is represented according to the model used by Amzel and Poljak (12). The disulfide bridge is shown and the RGD sequence is boxed in.

The peptide segment encoded by the exons II and III corresponds to a V type IgSF domain as described by Williams (13) including the β-strands A, B, C, C', C", D, E, F and G shown in FIG. 6, possessing two unusual features.

Firstly, this V-type domain includes an extra loop of approximately 30 amino acids encoded by the first part of the exon III. This loop shown in FIG. 4 joins the β-strand C to the β-strand C' and contains, in particular, ten proline residues. It seems that such an insertion might be compatible with a IgSF-type fold to the extent that it does not cause rupture of the central core of the fold that is considered to consist of the β-strands A, B, E and G, F, C as described by Lesk (14).

This extra loop acts as immunogen since it is probably exposed at the outside of the molecule and consequently is exposed to recognition by antibodies.

As a general rule the differences in the V-type and C-type domains appear in the middle of the Ig-type fold at this site, i.e. in the region of the C β-strand.

Furthermore, the insertion of a peptide structure encoded by a supplementary exon (15), forming an additional mini-loop, has been described in domain 4 of the N-CAM molecule.

The second unusual feature is that the cysteine downstream from domain 1 seems to be located in the β-strand G rather than in the β-strand F (residue 121), as is almost invariably the case. The sequence Asp-Gly-Tyr-Cys (SEQ ID NO:10) is located very characteristically in the β-strand F and is found here, except that an Ala residue replaces the Cys residue (FIG. 4). It seems possible that a disulfide bridge may be formed and, for example, it should be noted that an unusual disulfide bridge of a different kind has been oberved in the V-type domain of the α chain of CD8 as described by Kirszbaum (16).

An Arg-Gly-Asp (RGD) sequence is found in the β-strand E (FIG. 4). This sequence is known to represent a potential adhesiotope as described by Ruoslahti (17) but it has not been established whether it forms the core of an essential binding site since, in this position, such a sequence would probably be located within the IgSF-type fold.

The exons IV, V and VI code for IgSF-related domains as described by Williams (13) with 51, 50 and 42 amino acids, respectively, between the two conserved cysteine residues. These three domains possess C-type folds and show sequence patterns characteristic of the C2-type domain (13). They have been compared with sequences of the C2-type domain with the aid of the ALIGN program according to the method described by Dayhoff (18) and Williams (19). Of 57 sequences examined, scores greater than 3SD (standard deviations) were obtained 32, 41 and 11 times for domains 2, 3 and 4, respectively. Domain 4 belongs to the truncated C2-type domain in the sense that it does not possess the β-strand D.

The domains 1 and 2 of LAG-3 were aligned and compared by eye with the domains 3 and 4, taking into account identities and structural considerations.

FIG. 5 shows the internal homology of LAG-3.

The amino acid sequences of domain 1 (starting from position 91 in FIG. 5 (and in accordance with the numbering in FIG. 5) after the extra loop) and domain 2 were aligned with the corresponding positions in domains 3 and 4. The identities are indicated by (*) and the similarities by (.).

Since domain 1 contains a sequence forming an extra loop, the alignment was begun at amino acid 91 in this domain and at amino acid 276 in domain 3 of FIG. 5. Out of 129 possible matches between residues, 34 identities, 35 similarities and 9 breaks were observed (alignment score greater than +8.5 SD). Moreover, in the β-strand F of domains 2 and 4, there is a WxC sequence which is most unusual at this position where the sequence Y or FxC is usually found, as described by Williams (13). Taken together, these results suggest that LAG-3 has evolved by gene duplication from a pre-existing two-domain structure resembling that of an Ig L chain.

The sequences of LAG-3 and CD4 of the rat have also been aligned, as is shown in FIG. 6. The dotted lines above the sequences show the positions of the β-strands in the four IgSF-type domains. The leader sequence L and the transmembrane sequence (TM) are shown by a continuous line above the sequence. The position of the introns is shown by arrows above the sequence (for LAG-3) and below the sequence (for CD4) as described by Maddon (20) for human CD4. Two large gaps are inserted corresponding to the sequence of the extra loop in domain 1 of LAG-3 and in order to account for the fact that domain 3 of CD4 is a V-type domain, whereas domain V of LAG-3 is a C2-type domain. The fragments of similarity comprise the start of domain 1 (9 identities and 10 similarities out of 17 possible matches), and the very unusual sequence WxC in domains 2 and 4 of LAG-3, which are also present at the corresponding positions in CD4. This sequence pattern is not found in an equivalent position in any other IgSF-type domain. Overall, there are 87 identities and 82 similarities out of 338 aligned residues (19 sequence breaks) when the extra-cellular regions of LAG-3 and CD4 of the rat are compared. One of the principal features of LAG-3 is, consequently, its relationship to CD4.

As in the LAG-3 structure known fragments having internal sequence homologies have been found in the CD4 molecule between domains 1 and 3 as well as between domains 2 and 4. More generally, the exon/intron organisation of LAG-3 and CD4 is very similar: both genes comprise an intron within the first IgSF-type domain and the position of the introns (shown by arrows in FIG. 6) in LAG-3 is very similar to that of CD4.

It has been suggested that CD4 has evolved by gene duplication from a pre-existing structure with 2 IgSF-type domains. The present discovery strengthens this hypothesis and the inventors suggest, on the basis of similarities of sequence and exon/intron organisation, that CD4 and LAG-3 have thus shared a common 4-domain ancestor.

The LAG-3 protein may thus be expected to function as do many other molecules of the superfamily of the Ig type as ligand for a soluble protein or for a membrane protein. The known examples include proteins whose expression is positively regulated by cell activation such as ICAM-1, known to be involved in cell-cell interactions, or IL1-R and IL6-R which function as receptors for growth factors.

In view of the fact that the LAG-3 protein is expressed in substantial amounts on activated lymphocytes (probably more than 5000 sites per cell given the limits of detection of indirect techniques of immunofluorescence with a rabbit anti-serum in flow cytometry) and taking into account its homology with CD4, the very likely function of LAG-3 is one of intercellular adhesion. The characterization of the receptor-ligand couples (for example ICAM-1/LFA-1 or CD4/MHC, class II) in this domain is in progress. The CD4 molecule has been crystallized and its atomic structure deduced by X-ray analysis (Ryu (22) Wang (23)). The binding sites for anti-CD4 antibodies, binding sites for the gp120 protein of HIV (AIDS virus) and the binding sites for molecules of class II of the major histocompatibility complex (MHC) have been studied and it has become clear that the first NH$_2$-terminal domain (domain 1) is the most important for the functional activity of CD4. It has been shown that soluble CD4 molecules obtained by deletion of the transmembrane and cytoplasmic parts of the natural CD4 molecule either alone or coupled to constant regions of immunoglobulins (creation of a CD4 immunoadhesin (Byrn 24)) are capable of binding the gp120 protein and of preventing the dissemination of infection by HIV. Similarly, with respect to the ICAM-1 molecule, it has been shown that the first NH$_2$-terminal domain (domain 1) contains binding sites for LFA-1 and attachment sites for the rhinoviruses (Staunton (25)). Two therapeutic applications which follow from knowledge of the structure of ICAM-1 have been described. The expression of ICAM-1 is considerably enhanced at the surface of the bronchial epithelium during asthmatic disease and in a model of a cynomolgus monkey made asthmatic, it is possible to reduce the infiltration of the bronchi by eosinophil granulocytes and to improve the clinical state by intravenous injection of anti-ICAM antibodies (Wegner (26)). In respect to the utilization of a recombinant molecule made soluble by deletion of the transmembrane and cytoplasmic domains, it has been shown that the soluble ICAM-1 molecule inhibits the infection of human cells by rhinoviruses by blocking the attachment of the virus to the natural ICAM-1 molecule at the surface of the cells by competition (Marlin (27)).

In view of the structural analogies with CD4, it is thus possible that LAG-3 may be a site of entry for a virus. As regards the HIV or related viruses, one of the possible attachment sites may consist (by analogy with CD4) in this case of all or part of the following amino acid sequence including, in particular, the β-strand C" of domain V: Gly Leu Arg Ser Gly Arg Leu Pro Leu Gln Pro Arg Val Gln Leu Asp Glu Arg (corresponding to the amino acids 80 to 97 of the LAG-3 protein, SEQ ID NO:7). Moreover, the LAG-3 gene has been localized on chromosome 12 (band p 13.3) (Triebel (28)) close to CD4. The study of human-hamster hybrid cells has shown that cell proteins encoded in genes of the human chromosome 12 (genes different from CD4) were necessary and sufficient for the expression of the HIV genes (Hart (29)). The LAG-3 protein might thus be involved in the reproductive cycle of the HIV, resulting in the production of infectious virions, independently of its possible capacity to act as receptor for the HIV.

Finally, structural homologies exist between the cytoplasmic region of the LAG-3 protein (in particular in the region of the peptide Arg Arg Gln Trp Arg Pro Arg Arg Phe Ser corresponding to amino acid residues 447 to 456 of SEQ ID NO:7) and various proteins encoded in the HIV genome, such as for example the REV protein (Yourno (30)) or FIV (Ratner (31)). These homology relationships suggest there again that the LAG-3 protein expressed by activated lymphocytes might play a role in the phases of replication or in the production of infectious viral particles of the HIV.

IX—Detection of the Natural LAG-3 Molecule

Anti-LAG-3 rabbit antibodies were obtained after repeated injections of a synthetic peptide coupled to KLH into rabbits. This peptide comprises 30 amino acids forming the sequence shown in the sequence SEQ ID No3 included in the extra loop of domain V of LAG-3.

After labelling of the membrane proteins of T cells activated by phytohemagglutinin with $^{125}I$, immunoprecipitation by specific rabbit antibodies and purification on SDS-polyacrylanide gel, a single band of about 55 k, daltons was detected under reducing and non-reducing conditions (FIG. 7). This observed molecular mass of about 55 k daltons would correspond to the molecular mass derived from the analysis of the translation of the 1AG-3 protein (51 k daltons) to which are added about 5 k daltons due to the presence of sugars (in particular at some of the 4 N-glycosylation sites), making the natural LAG-3 protein a membrane glycoprotein.

The LAG-3 protein does exist in the form of a single chain, probably glycosylated, at the surface of the T cells.

X—In vitro Transcription and Translation of the LAG-3 Gene

In order to conclusively define the coding region and establish the capacity to be translated of the mRNA obtained by transcription of the FDC sequence, we have transcribed both strands of the FDC cDNA (Fco 47 III - BglII 209–1829 bp fragment) by using either the T3 or the T7 RNA polymerase using as substrate the FDC clone in the pBS vector. The two RNA preparations were then translated in vitro by using a rabbit reticulocyte extract in the presence of methionine $^{35}S$. The sense RNA containing the poly-A tail at the 3' end was translated into a protein of molecular mass of 55,000 daltons which could be detected by autoradiography after migration in a gel of the SDS-PAGE type. This estimated molecular mass is very similar to the theoretical molecular mass of 54457 corresponding to the 498 amino acids of the LAG-3 polypeptide with an intact, uncleaved signal peptide. No translation product larger than 20,000 daltons could be detected using the anti-sense LAG-3 RNA as substrate in the reaction with the rabbit reticulocyte extract.

XI—Expression of a Transmembrane Recombinant LAG-3 Protein (LAG 3-C) and a Soluble Recombinant LAG-3 Protein (LAG 3-S)

We have employed a system using a vector of the "baculovirus" type. This system makes it possible to produce proteins of an insect (Spodoptera Frugiperda) foreign to the cells (SF9 cells) by using in vivo recombination between a transfer vector (plasmid p PVL 941) which contains the foreign gene, on the one hand, and the genome of a virus (Autographa Californica Nuclear Polyhedrosis virus AcMNPV), on the other. The viral genome is placed under the strong control of the promoter for the gene of the protein called polyhedrin. This system was described by Luckow (21) after transfection of the recombinant plasmid and the viral genome; the SF9 cells are selected by successive purifications (screening of recombinants), thus making possible the production of considerable amounts of recombinant protein. This protein is normally cleaved (the hydrophobic signal peptide is removed inside the cell) and glycosylated (at least partially).

1) Construction of the transfer vector a) Preparation of the vector

The schema for the preparation of the vector is shown in FIG. 8.

The vector PVL941 (obtainable from Dr. Max SUMMERS, University of Texas, U.S.A.) was cut by the restriction enzyme BamHI, then dephosphorylated by calf intestine phosphatase. This was done in order to prevent the autoligation of the vector with itself.

We then prepared from the FDC CDNA clone a fragment of 1620 base pairs resulting from digestion by the enzymes EC047 III (position 209 of FDC) and BglII (position 1829 of FDC). The ends cut, on the one hand, by the enzyme Eco47III and by the enzyme BglII on the other, were made blunt by a synthetic reaction with a Klenow DNA polymerase (T4 DNA polymerase). A double-stranded oligonucleotide "linker" containing a BglII restriction site was then attached to the Eco47III BglII FDC fragment in order to create the construction LAG 3-C (C for complete) and a linker containing a BamHI site was attached in order to create the construction LAG 3-S (S for soluble). After ligation, digestion was performed with an excess of restriction enzyme of the BglII type (in the case of the construction LAG 3-C) or of the BamHI type (in the case of the construction LAG 3-S), then the fragments corresponding to the 2 constructions were purified by gel electrophoresis. The last step consisted of linking the BglII LAG 3-C fragment or the BamHI LAG 3-S fragment to the vector PVL 941-BamHI.

b) Selection and amplification of the recombinant vectors

Competent JM109 bacteria were transformed with the recombinant transfer vector containing one or other of the constructions. Colonies resistant to ampicillin were placed in culture, then the plasmid DNA contained in these bacteria was purified; in this way, a number of clones containing the transfer vector was obtained and clones containing the LAG 3-C fragment or the LAG 3-S fragment in the right orientation were selected. In order to obtain the recombined plasmid in the pure state, capable of being used in transfection experiments, the clone of bacteria thus obtained was placed in culture in 500 ml of medium with ampicillin, then the plasmid was purified on a cesium chloride gradient.

c) Purification of genomic DNA of the virus

This was done according to the method described in "A manual of methods for Baculovirus vectors and insect cell culture procedures" provided by Dr. Max SUMMERS of the University of Texas, U.S.A.

d) Transfection of cells with the recombinant vector containing the LAG 3-C or LAG 3-S insert and the genome of the virus.

It concerns the co-transfection of SF9 cells with, on the one hand, the purified recombinant vector and the viral genome on the other using the calcium chloride method. This was done in accordance with the conditions described in the manual referred to in c).

e) Selection of the recombined viruses

5 Days after transfection, the supernatants of the SF9 cells were recovered, then assayed. These assays are performed by infecting fresh SF9 cells with successive dilutions of this primary culture supernatant. Initially, there are considered to be $10^7$ pfu/ml (pfu="plaque forming unit") and successive dilutions are made so as to obtain between 100 and 1 pfu/ml. After 3 days, the SF9 cells thus infected are assayed by the "dot blot" hybridization procedure. The cells are lysed with NaOH, transferred to nylon and hybridized with a probe corresponding to the FDC fragment of 1871 base pairs. After washing and autoradiography, the positive wells are located and the wells corresponding to the highest dilutions are retained. This screening technique is performed a second and third time. During the third screening, a check is made that the dots giving a positive signal in "dot blot" hybridization do not contain SF9 cells containing inclusions. These inclusions correspond to the secretion of the protein polyhedrin, produced after infection of SF9 cells by a non-recombined, wild-type virus. This last point was also checked not by direct reading of the plaque but by a procedure involving collection of the cells, spreading them on a glass slide and staining with May-Grünwald-Giemsa.

f) Detection of the recombinant protein LAG 3-C and LAG 3-S

Figure 9:
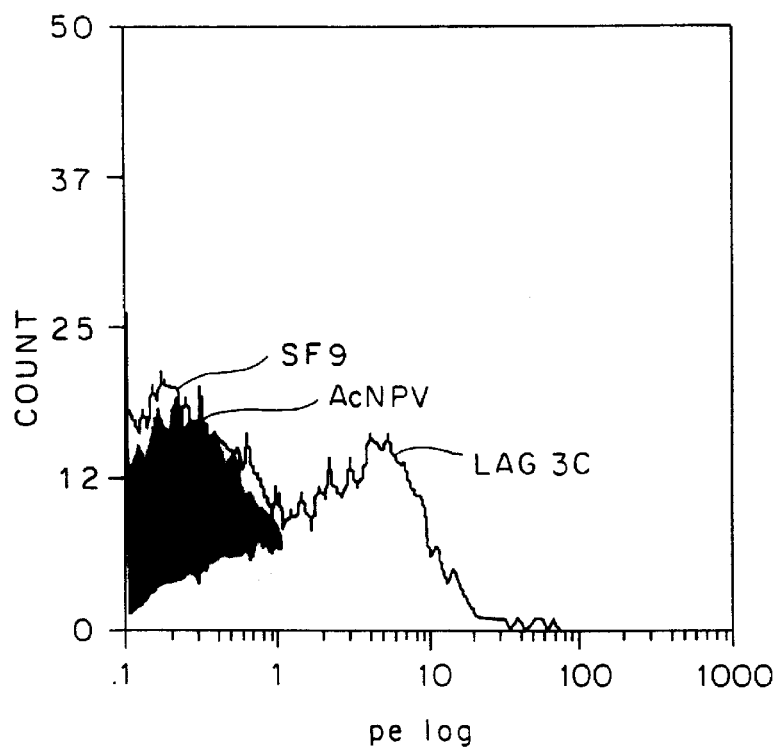
Figure 10:
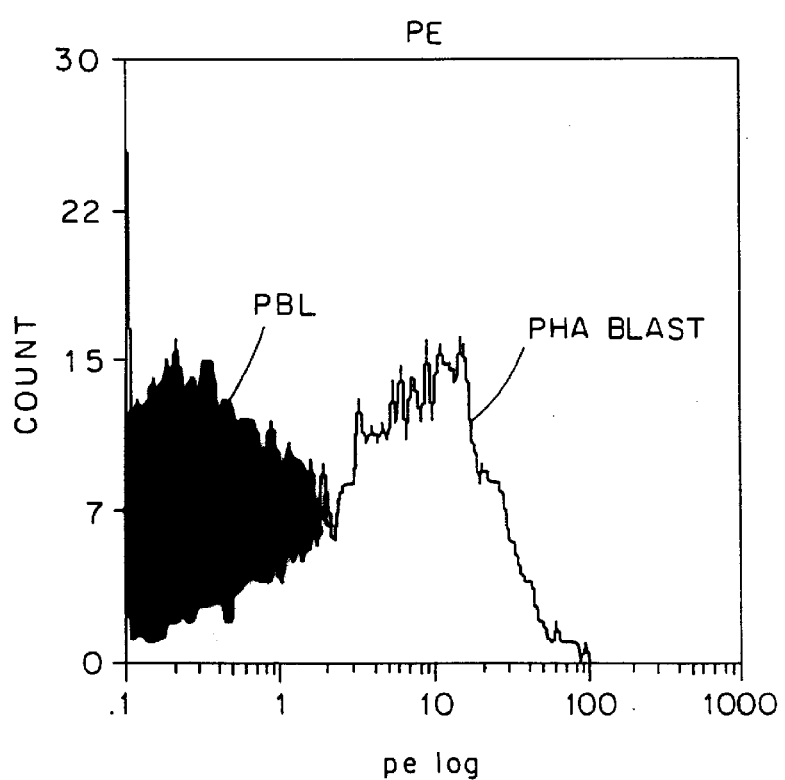

SF9 cells infected with the recombinant viral clone containing the LAG 3-C fragment were obtained on the 5th day of culture after an infection at 0.1 pfu/cell. These SF9 cells express the recombinant LAG-3 molecule at the surface as is shown by the immunofluorescent reactivity of the specific rabbit antibody, compared with the reactivity obtained with uninfected SF9 cells or SF9 cells infected with a AcNPV wild-type virus (FIG. 9). Furthermore, the reactivity of the LAG-3-specific rabbit serum towards the SF9 cells expressing LAG-3 was compared with the reactivity obtained towards T lymphocytes activated by phytohemagglutinin (PHA-blasts). The histograms obtained are similar and thus show that the number of recombinant LAG-3 molecules (FIG. 9) expressed at the surface of the SF9 cells is comparable to the number of natural LAG-3 molecules expressed at the surface of the activated lymphocytes (FIG. 10).

Figure 11:
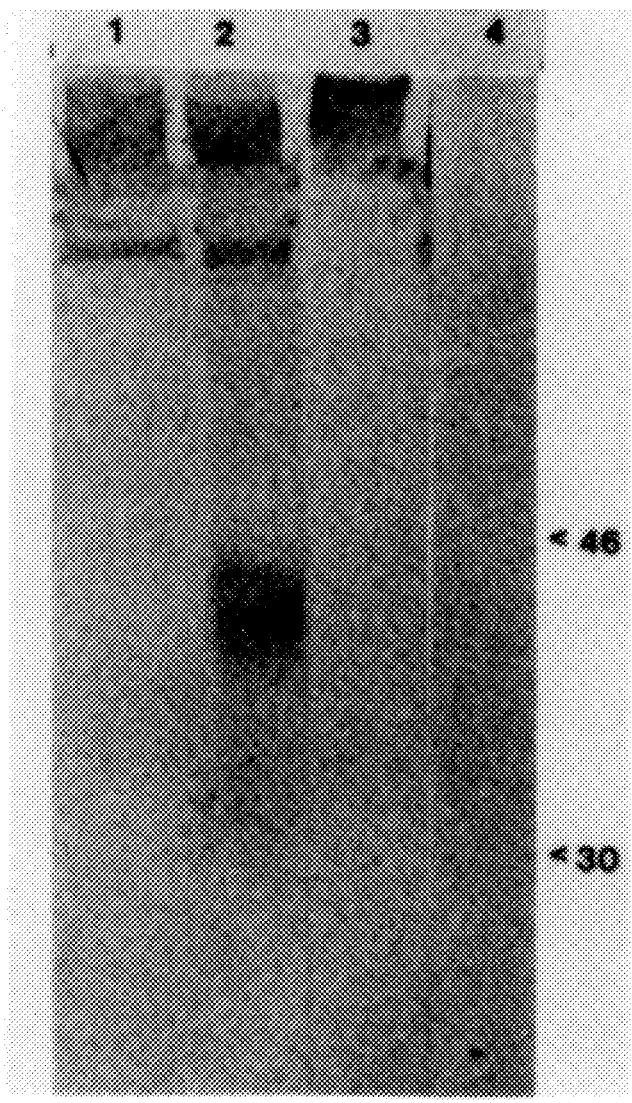

Supernatants of SF9 cells infected with the recombinant viral clone containing the LAG 3-S fragment were obtained on the 5th day of culture after an infection at 0.1 pfu/cell. A supernatant was assayed by the so-called "Western blot" technique with the anti-loop anti-peptide antibodies of domain V described in section IX. A pure signal corresponding to a protein of about 45 kd was obtained after revelation with anti-rabbit goat antibodies labelled with peroxidase (FIG. 11).

This molecular mass corresponds well with the mass expected of the LAG 3-S Eco47 III-BamHI fusion protein (38038 K daltons) after glycosylation in the SF9 cells.

The structure of the part coding for LAG 3-S (SEQ ID No.5) shows that the first three domains of LAG-3 (upstream from the internal BamHI site) were fused with a nucleotide segment of 56 base pairs of the gene for polyhedrin downstream from the BamHI site. In total, after cleavage of the signal peptide of 28 amino acids, the fusion protein comprises 352 amino acids, 335 corresponding to LAG-3 and 17 being derived from one of the reading frames of the gene for polyhedrin.

REFERENCES

1. Nowill, A. et al., J. Exp. Med. 163, 1601.
2. Maniatis, T. et al., 1982. Molecular cloning: A laboratory manual, Cold spring harbor laboratory New York.
3. Mechler, B. et al., J. Cell Biol. 88, 29 (1981).
4. Aviv et al., Proc. Natl. Acad. Sci. USA 69 : 1408.
5. Triebel, F. et al., Eur. J. Immunol. 17, 1209.
6. Gubler, U. et al., Gene. 25, 263.
7. Davis, M. M. et al., Proc. Natl. Acad. Sci. USA. 81:2194.
8. Huynh, T. V. et al., DNA cloning: A practical approach. 49–78, D. Glover Editor. IRL Press. Oxford. United Kingdom.
9. Sanger, F. et al., Proc. Natl. Acad. Sci. USA 75, 5463.
10. Dariavach, P. et al., Proc. Natl. Acad. Sci. USA. 84, 9074.
11. Feinberg, A. P. et al., Anal. Biochem. 132, 6.
12. Amzel, L. M. et al., Ann. Rev. Biochem 48, 961 (1979).
13. Williams, A. F. Immunol. Today 8, 298 (1987).
14. Lesk, A. M. & Chothia, C. J. Mol. Biol. 160, 325 (1982).
15. Santoni, M. J. et al. EMBO J. 8, 395 (1989).
16. Kirszbaum, L. et al., J. Immunol. 142, 3931 (1989).
17. Ruoslahti, E. et al., M. D. Cell 44, 517 (1986).
18. Dayhoff, M. O. et al., Enzymol. 91, 524 (1983).
19. Williams, A. F. et al., Ann. Rev. Immunol. 6, 381.
20. Maddon, P. J. et al. Proc. Natl. Acad. Sci. USA 84, 9155 (1987).
21. Luckow, V. A. et al., Bio/Technology, 6:47.
22. Ryu S. E. et al., Nature, 348, 419.
23. Wang J. et al., Nature, 348, 411
24. Byrn R. A. et al., Nature 344, 667
25. Staunton D. E. et al., Cell. 61, 243

26. Weginer C. D. et al., Science 247, 456
27. Marlin S. D. et al., Nature 344, 70
28. Triebel F. et al;, J. Exp. Med., 171, 1393
29. Hart E. C. et al., Science, 240, 483
30. Yourno J. et al., AIDS Res. Hum. Retroviruses 4:165–173(1988).
31. Ratner L. et al., Nature 313:277–284 (1985).

| Symbols of the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. A peptide, which is the soluble portion of the LAG-3 protein, having the amino acid sequence of residues 1–420 of SEQ ID NO:7, or a fragment thereof selected from the group consisting of:

residues 1 to 142 of SEQ ID NO:7;
residues 143 to 232 of SEQ ID NO:7;
residues 233 to 342 of SEQ ID NO:7;
residues 343 to 413 of SEQ ID NO:7; and
residues 42 to 71 of SEQ ID NO:7.

2. A peptide, which is the soluble portion of the LAG-3 protein having the amino acid sequence of residues 1 to 420 of SEQ ID NO:7 with an added methionine residue immediately N-terminal to amino acid residue 1 of SEQ ID NO:7, or a fragment thereof consisting of residues 1 to 142 of SEQ ID NO:7 with an added methionine residue immediately N-terminal to amino acid residue 1 of SEQ ID NO:7.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1871 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 231..1724

( x i ) SEQUENCE DESCRIPTION: SEQ ID NO:1:

```
TCAGGCTGCC  TGATCTGCCC  AGCTTTCCAG  CTTTCCTCTG  GATTCCGGCC  TCTGGTCATC        60

CCTCCCCACC  CTCTCTCCAA  GGCCCTCTCC  TGGTCTCCCT  TCTTCTAGAA  CCCCTTCCTC       120

CACCTCCCTC  TCTGCAGAAC  TTCTCCTTTA  CCCCCCACCC  CCCACCACTG  CCCCCTTTCC       180

TTTTCTGACC  TCCTTTTGGA  GGGCTCAGCG  CTGCCCAGAC  CATAGGAGAG  ATG  TGG          236
                                                           Met  Trp
                                                           -28

GAG  GCT  CAG  TTC  CTG  GGC  TTG  CTG  TTT  CTG  CAG  CCG  CTT  TGG  GTG  GCT    284
Glu  Ala  Gln  Phe  Leu  Gly  Leu  Leu  Phe  Leu  Gln  Pro  Leu  Trp  Val  Ala
     -25                      -20                      -15

CCA  GTG  AAG  CCT  CTC  CAG  CCA  GGG  GCT  GAG  GTC  CCG  GTG  GTG  TGG  GCC    332
Pro  Val  Lys  Pro  Leu  Gln  Pro  Gly  Ala  Glu  Val  Pro  Val  Val  Trp  Ala
-10                           -5                     1                    5

CAG  GAG  GGG  GCT  CCT  GCC  CAG  CTC  CCC  TGC  AGC  CCC  ACA  ATC  CCC  CTC    380
Gln  Glu  Gly  Ala  Pro  Ala  Gln  Leu  Pro  Cys  Ser  Pro  Thr  Ile  Pro  Leu
               10                           15                   20

CAG  GAT  CTC  AGC  CTT  CTG  CGA  AGA  GCA  GGG  GTC  ACT  TGG  CAG  CAT  CAG    428
Gln  Asp  Leu  Ser  Leu  Leu  Arg  Arg  Ala  Gly  Val  Thr  Trp  Gln  His  Gln
          25                           30                   35

CCA  GAC  AGT  GGC  CCG  CCC  GCT  GCC  GCC  CCC  GGC  CAT  CCC  CTG  GCC  CCC    476
Pro  Asp  Ser  Gly  Pro  Pro  Ala  Ala  Ala  Pro  Gly  His  Pro  Leu  Ala  Pro
```

```
                       40                           45                              50
GGC  CCT  CAC  CCG  GCG  GCG  CCC  TCC  TCC  TGG  GGG  CCC  AGG  CCC  CGC  CGC       524
Gly  Pro  His  Pro  Ala  Ala  Pro  Ser  Ser  Trp  Gly  Pro  Arg  Pro  Arg  Arg
 55                     60                        65                         70

TAC  ACG  GTG  CTG  AGC  GTG  GGT  CCC  GGA  GGC  CTG  CGC  AGC  GGG  AGG  CTG       572
Tyr  Thr  Val  Leu  Ser  Val  Gly  Pro  Gly  Gly  Leu  Arg  Ser  Gly  Arg  Leu
                         75                   80                        85

CCC  CTG  CAG  CCC  CGC  GTC  CAG  CTG  GAT  GAG  CGC  GGC  CGG  CAG  CGC  GGG       620
Pro  Leu  Gln  Pro  Arg  Val  Gln  Leu  Asp  Glu  Arg  Gly  Arg  Gln  Arg  Gly
                    90                        95                       100

GAC  TTC  TCG  CTA  TGG  CTG  CGC  CCA  GCC  CGG  CGC  GCG  GAC  GCC  GGC  GAG       668
Asp  Phe  Ser  Leu  Trp  Leu  Arg  Pro  Ala  Arg  Arg  Ala  Asp  Ala  Gly  Glu
               105                      110                       115

TAC  CGC  GCC  GCG  GTG  CAC  CTC  AGG  GAC  CGC  GCC  CTC  TCC  TGC  CGC  CTC       716
Tyr  Arg  Ala  Ala  Val  His  Leu  Arg  Asp  Arg  Ala  Leu  Ser  Cys  Arg  Leu
          120                      125                       130

CGT  CTG  CGC  CTG  GGC  CAG  GCC  TCG  ATG  ACT  GCC  AGC  CCC  CCA  GGA  TCT       764
Arg  Leu  Arg  Leu  Gly  Gln  Ala  Ser  Met  Thr  Ala  Ser  Pro  Pro  Gly  Ser
135                      140                       145                       150

CTC  AGA  GCC  TCC  GAC  TGG  GTC  ATT  TTG  AAC  TGC  TCC  TTC  AGC  CGC  CCT       812
Leu  Arg  Ala  Ser  Asp  Trp  Val  Ile  Leu  Asn  Cys  Ser  Phe  Ser  Arg  Pro
                         155                      160                       165

GAC  CGC  CCA  GCC  TCT  GTG  CAT  TGG  TTC  CGG  AAC  CGG  GGC  CAG  GGC  CGA       860
Asp  Arg  Pro  Ala  Ser  Val  His  Trp  Phe  Arg  Asn  Arg  Gly  Gln  Gly  Arg
               170                      175                       180

GTC  CCT  GTC  CGG  GAG  TCC  CCC  CAT  CAC  CAC  TTA  GCG  GAA  AGC  TTC  CTC       908
Val  Pro  Val  Arg  Glu  Ser  Pro  His  His  His  Leu  Ala  Glu  Ser  Phe  Leu
          185                      190                       195

TTC  CTG  CCC  CAA  GTC  AGC  CCC  ATG  GAC  TCT  GGG  CCC  TGG  GGC  TGC  ATC       956
Phe  Leu  Pro  Gln  Val  Ser  Pro  Met  Asp  Ser  Gly  Pro  Trp  Gly  Cys  Ile
200                      205                       210

CTC  ACC  TAC  AGA  GAT  GGC  TTC  AAC  GTC  TCC  ATC  ATG  TAT  AAC  CTC  ACT      1004
Leu  Thr  Tyr  Arg  Asp  Gly  Phe  Asn  Val  Ser  Ile  Met  Tyr  Asn  Leu  Thr
215                      220                       225                       230

GTT  CTG  GGT  CTG  GAG  CCC  CCA  ACT  CCC  TTG  ACA  GTG  TAC  GCT  GGA  GCA      1052
Val  Leu  Gly  Leu  Glu  Pro  Pro  Thr  Pro  Leu  Thr  Val  Tyr  Ala  Gly  Ala
                         235                      240                       245

GGT  TCC  AGG  GTG  GGG  CTG  CCC  TGC  CGC  CTG  CCT  GCT  GGT  GTG  GGG  ACC      1100
Gly  Ser  Arg  Val  Gly  Leu  Pro  Cys  Arg  Leu  Pro  Ala  Gly  Val  Gly  Thr
               250                      255                       260

CGG  TCT  TTC  CTC  ACT  GCC  AAG  TGG  ACT  CCT  CCT  GGG  GGA  GGC  CCT  GAC      1148
Arg  Ser  Phe  Leu  Thr  Ala  Lys  Trp  Thr  Pro  Pro  Gly  Gly  Gly  Pro  Asp
          265                      270                       275

CTC  CTG  GTG  ACT  GGA  GAC  AAT  GGC  GAC  TTT  ACC  CTT  CGA  CTA  GAG  GAT      1196
Leu  Leu  Val  Thr  Gly  Asp  Asn  Gly  Asp  Phe  Thr  Leu  Arg  Leu  Glu  Asp
280                      285                       290

GTG  AGC  CAG  GCC  CAG  GCT  GGG  ACC  TAC  ACC  TGC  CAT  ATC  CAT  CTG  CAG      1244
Val  Ser  Gln  Ala  Gln  Ala  Gly  Thr  Tyr  Thr  Cys  His  Ile  His  Leu  Gln
295                      300                       305                       310

GAA  CAG  CAG  CTC  AAT  GCC  ACT  GTC  ACA  TTG  GCA  ATC  ATC  ACA  GTG  ACT      1292
Glu  Gln  Gln  Leu  Asn  Ala  Thr  Val  Thr  Leu  Ala  Ile  Ile  Thr  Val  Thr
                         315                      320                       325

CCC  AAA  TCC  TTT  GGG  TCA  CCT  GGA  TCC  CTG  GGG  AAG  CTG  CTT  TGT  GAG      1340
Pro  Lys  Ser  Phe  Gly  Ser  Pro  Gly  Ser  Leu  Gly  Lys  Leu  Leu  Cys  Glu
               330                      335                       340

GTG  ACT  CCA  GTA  TCT  GGA  CAA  GAA  CGC  TTT  GTG  TGG  AGC  TCT  CTG  GAC      1388
Val  Thr  Pro  Val  Ser  Gly  Gln  Glu  Arg  Phe  Val  Trp  Ser  Ser  Leu  Asp
          345                      350                       355

ACC  CCA  TCC  CAG  AGG  AGT  TTC  TCA  GGA  CCT  TGG  CTG  GAG  GCA  CAG  GAG      1436
Thr  Pro  Ser  Gln  Arg  Ser  Phe  Ser  Gly  Pro  Trp  Leu  Glu  Ala  Gln  Glu
```

```
                    360                      365                       370
GCC  CAG  CTC  CTT  TCC  CAG  CCT  TGG  CAA  TGC  CAG  CTG  TAC  CAG  GGG  GAG    1484
Ala  Gln  Leu  Leu  Ser  Gln  Pro  Trp  Gln  Cys  Gln  Leu  Tyr  Gln  Gly  Glu
375                      380                      385                      390

AGG  CTT  CTT  GGA  GCA  GCA  GTG  TAC  TTC  ACA  GAG  CTG  TCT  AGC  CCA  GGT    1532
Arg  Leu  Leu  Gly  Ala  Ala  Val  Tyr  Phe  Thr  Glu  Leu  Ser  Ser  Pro  Gly
                         395                      400                      405

GCC  CAA  CGC  TCT  GGG  AGA  GCC  CCA  GGT  GCC  CTC  CCA  GCA  GGC  CAC  CTC    1580
Ala  Gln  Arg  Ser  Gly  Arg  Ala  Pro  Gly  Ala  Leu  Pro  Ala  Gly  His  Leu
               410                      415                      420

CTG  CTG  TTT  CTC  ACC  CTT  GGT  GTC  CTT  TCT  CTG  CTC  CTT  TTG  GTG  ACT    1628
Leu  Leu  Phe  Leu  Thr  Leu  Gly  Val  Leu  Ser  Leu  Leu  Leu  Leu  Val  Thr
               425                      430                      435

GGA  GCC  TTT  GGC  TTT  CAC  CTT  TGG  AGA  AGA  CAG  TGG  CGA  CCA  AGA  CGA    1676
Gly  Ala  Phe  Gly  Phe  His  Leu  Trp  Arg  Arg  Gln  Trp  Arg  Pro  Arg  Arg
          440                      445                      450

TTT  TCT  GCC  TTA  GAG  CAA  GGG  ATT  CAC  CCT  CGC  AGG  CTC  AGA  GCA  AGA    1724
Phe  Ser  Ala  Leu  Glu  Gln  Gly  Ile  His  Pro  Arg  Arg  Leu  Arg  Ala  Arg
455                      460                      465                      470

TAGAGGAGCT  GGAGCAAGAA  CCGGAGCCGG  AGCCGGAGCC  GGAACCGGAG  CCCGAGCCCG            1784

AGCCCGAGCC  GGAGCAGCTC  TGACCTGGAG  CTGAGGCAGC  CAGCAGATCT  CAGCAGCCCA            1844

GTCCAAATAA  ACGTCCTGTC  TAGCAGC                                                   1871
```

( 2 ) INFORMATION FOR SEQ ID NO:2:

( i ) SEQUENCE CHARACTERISTICS:
        ( A ) LENGTH: 471 amino acids
        ( B ) TYPE: amino acid
        ( D ) TOPOLOGY: linear ( i i ) MOLECULE TYPE: protein ( i x ) FEATURE:
        ( A ) NAME/KEY: Peptide
        ( B ) LOCATION: 1
        ( D ) OTHER INFORMATION: /note= "Hydrogen is present at the
             N- terminus"

( x i ) SEQUENCE DESCRIPTION: SEQ ID NO:2:

```
                                                  Met  Val  Pro  Val  Val
                                                   1                    5

Trp  Ala  Gln  Glu  Gly  Ala  Pro  Ala  Gln  Leu  Pro  Cys  Ser  Pro  Thr  Ile
                    10                       15                       20

Pro  Leu  Gln  Asp  Leu  Ser  Leu  Leu  Arg  Arg  Ala  Gly  Val  Thr  Trp  Gln
                    25                       30                       35

His  Gln  Pro  Asp  Ser  Gly  Pro  Pro  Ala  Ala  Ala  Pro  Gly  His  Pro  Leu
               40                       45                       50

Ala  Pro  Gly  Pro  His  Pro  Ala  Ala  Pro  Ser  Ser  Trp  Gly  Pro  Arg  Pro
          55                       60                       65

Arg  Arg  Tyr  Thr  Val  Leu  Ser  Val  Gly  Pro  Gly  Leu  Arg  Ser  Gly
70                       75                       80                       85

Arg  Leu  Pro  Leu  Gln  Pro  Arg  Val  Gln  Leu  Asp  Glu  Arg  Gly  Arg  Gln
               90                       95                       100

Arg  Gly  Asp  Phe  Ser  Leu  Trp  Leu  Arg  Pro  Ala  Arg  Arg  Ala  Asp  Ala
               105                      110                      115

Gly  Glu  Tyr  Arg  Ala  Ala  Val  His  Leu  Arg  Asp  Arg  Ala  Leu  Ser  Cys
               120                      125                      130

Arg  Leu  Arg  Leu  Arg  Leu  Gly  Gln  Ala  Ser  Met  Thr  Ala  Ser  Pro  Pro
               135                      140                      145
```

```
Gly  Ser  Leu  Arg  Ala  Ser  Asp  Trp  Val  Ile  Leu  Asn  Cys  Ser  Phe  Ser
150            155                      160                      165

Arg  Pro  Asp  Arg  Pro  Ala  Ser  Val  His  Trp  Phe  Arg  Asn  Arg  Gly  Gln
               170                      175                      180

Gly  Arg  Val  Pro  Val  Arg  Glu  Ser  Pro  His  His  His  Leu  Ala  Glu  Ser
               185                      190                      195

Phe  Leu  Phe  Leu  Pro  Gln  Val  Ser  Pro  Met  Asp  Ser  Gly  Pro  Trp  Gly
               200                      205                      210

Cys  Ile  Leu  Thr  Tyr  Arg  Asp  Gly  Phe  Asn  Val  Ser  Ile  Met  Tyr  Asn
215                      220                      225

Leu  Thr  Val  Leu  Gly  Leu  Glu  Pro  Pro  Thr  Pro  Leu  Thr  Val  Tyr  Ala
230                      235                      240                      245

Gly  Ala  Gly  Ser  Arg  Val  Gly  Leu  Pro  Cys  Arg  Leu  Pro  Ala  Gly  Val
               250                      255                      260

Gly  Thr  Arg  Ser  Phe  Leu  Thr  Ala  Lys  Trp  Thr  Pro  Pro  Gly  Gly  Gly
               265                      270                      275

Pro  Asp  Leu  Leu  Val  Thr  Gly  Asp  Asn  Gly  Asp  Phe  Thr  Leu  Arg  Leu
               280                      285                      290

Glu  Asp  Val  Ser  Gln  Ala  Gln  Ala  Gly  Thr  Tyr  Thr  Cys  His  Ile  His
295                      300                      305

Leu  Gln  Glu  Gln  Gln  Leu  Asn  Ala  Thr  Val  Thr  Leu  Ala  Ile  Ile  Thr
310                      315                      320                      325

Val  Thr  Pro  Lys  Ser  Phe  Gly  Ser  Pro  Gly  Ser  Leu  Gly  Lys  Leu  Leu
               330                      335                      340

Cys  Glu  Val  Thr  Pro  Val  Ser  Gly  Gln  Glu  Arg  Phe  Val  Trp  Ser  Ser
               345                      350                      355

Leu  Asp  Thr  Pro  Ser  Gln  Arg  Ser  Phe  Ser  Gly  Pro  Trp  Leu  Glu  Ala
               360                      365                      370

Gln  Glu  Ala  Gln  Leu  Leu  Ser  Gln  Pro  Trp  Gln  Cys  Gln  Leu  Tyr  Gln
               375                      380                      385

Gly  Glu  Arg  Leu  Leu  Gly  Ala  Ala  Val  Tyr  Phe  Thr  Glu  Leu  Ser  Ser
390                      395                      400                      405

Pro  Gly  Ala  Gln  Arg  Ser  Gly  Arg  Ala  Pro  Gly  Ala  Leu  Pro  Ala  Gly
               410                      415                      420

His  Leu  Leu  Leu  Phe  Leu  Thr  Leu  Gly  Val  Leu  Ser  Leu  Leu  Leu  Leu
               425                      430                      435

Val  Thr  Gly  Ala  Phe  Gly  Phe  His  Leu  Trp  Arg  Arg  Gln  Trp  Arg  Pro
               440                      445                      450

Arg  Arg  Phe  Ser  Ala  Leu  Glu  Gln  Gly  Ile  His  Pro  Arg  Arg  Leu  Arg
               455                      460                      465

Ala  Arg
470
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:3:

```
Gly  Pro  Pro  Ala  Ala  Ala  Pro  Gly  His  Pro  Leu  Ala  Pro  Gly  Pro  His
1                   5                        10                       15

Pro  Ala  Ala  Pro  Ser  Ser  Trp  Gly  Pro  Arg  Pro  Arg  Arg  Tyr
               20                       25
```

( 2 ) INFORMATION FOR SEQ ID NO:4:

( i ) SEQUENCE CHARACTERISTICS:
        ( A ) LENGTH: 999 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CCTGCAATGT  CATTCTTTGA  GCTCAGTTCC  TCATCTCTGT  CATGGAGAGC  ATTAGATTTC      60
ATGAATTCAT  ACTAAGTGTC  CAATACAGTG  CTTAGCACGT  AATGAAGCCT  CAATACAATG     120
TAGTTATTCT  CCATGCCCCA  CAAAGCTGCA  TGCCTAGCCT  CAGACCTACC  ATTTTTTGGG    180
GTGCAGTAAG  GCTTCCTGTC  CACCATGTTC  CCAGGGACAT  TGTACTGATG  GGTGGAAAGG    240
CAGGTCTAAA  GGGGTCACGA  AGTTCTGGGA  GGTTAAGGGA  ACGAGGAAGG  AGATTGAGCA    300
ACAAGGAAAG  AGCTTGCCAA  GAAGGAGGTG  TGAATATTGG  GACTGAGGAG  GCAGCTTAGA    360
GATGGGCAAG  GGGGCAGTTC  CAGGCAGAAA  TGGTTCGTGG  AGGCAGAAGG  TCCCTGGGAG    420
AGGGAGCAGT  CTGGAGGGTG  GGGCAGGGGC  GAGGAGGGGG  AGGTGGGGAG  ACCCAGGACT    480
GAGGAAGTAA  ACAAGGGGAG  CGCCACCACA  GAGGTGGAGA  GGTGGAGGGT  GCTGCTGCTG    540
GGAATCAACC  CCCTCAGACT  TTCCACTGCG  AAGCGAAACC  GTAAGCCCTG  GGGTGCGGGG    600
GGCGGGCCGG  GAGGAGGGGA  AGTGGGGAAG  GTGGAGGGAA  GGCCGGGCAC  AGGGGTGAAG    660
GCCCAGAGAC  CAGCAGAACG  GCATCCCAGC  CACGACGGCC  ACTTTGCTCT  GTCTGCTGTC    720
CGCCACGGCC  CTGCTCTGTT  CCCTGGGACA  CCCCCGCCCC  CACCTCCTCA  GGCTGCCTGA    780
TCTGCCCAGC  TTTCCAGCTT  TCCTCTGGAT  TCCGGCCTCT  GGTCATCCCT  CCCCACCCTC    840
TCTCCAAGGC  CCTCTCCTGG  TCTCCCTTCT  TCTAGAACCC  CTTCCTCCAC  CTCCCTCTCT    900
GCAGAACTTC  TCCTTTCCCC  CCACCCCCCA  CCACTGCCCC  CTTTCCTTTT  CTGACCTCCT    960
TTTGGAGGGC  TCAGCGCTGC  CCAGACCATA  GGAGAGATG                              999
```

( 2 ) INFORMATION FOR SEQ ID NO:5:

( i ) SEQUENCE CHARACTERISTICS:
        ( A ) LENGTH: 1164 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 22..1161

( x i ) SEQUENCE DESCRIPTION: SEQ ID NO:5:

```
GCTGCCCAGA  CCATAGGAGA  G  ATG  TGG  GAG  GCT  CAG  TTC  CTG  GGC  TTG  CTG      51
                           Met  Trp  Glu  Ala  Gln  Phe  Leu  Gly  Leu  Leu
                            1              5                           10

TTT  CTG  CAG  CCG  CTT  TGG  GTG  GCT  CCA  GTG  AAG  CCT  CTC  CAG  CCA  GGG     99
Phe  Leu  Gln  Pro  Leu  Trp  Val  Ala  Pro  Val  Lys  Pro  Leu  Gln  Pro  Gly
               15                      20                          25

GCT  GAG  GTC  CCG  GTG  GTG  TGG  GCC  CAG  GAG  GGG  GCT  CCT  GCC  CAG  CTC    147
Ala  Glu  Val  Pro  Val  Val  Trp  Ala  Gln  Glu  Gly  Ala  Pro  Ala  Gln  Leu
               30                      35                          40

CCC  TGC  AGC  CCC  ACA  ATC  CCC  CTC  CAG  GAT  CTC  AGC  CTT  CTG  CGA  AGA    195
Pro  Cys  Ser  Pro  Thr  Ile  Pro  Leu  Gln  Asp  Leu  Ser  Leu  Leu  Arg  Arg
               45                      50                          55

GCA  GGG  GTC  ACT  TGG  CAG  CAT  CAG  CCA  GAC  AGT  GGC  CCG  CCC  GCT  GCC    243
Ala  Gly  Val  Thr  Trp  Gln  His  Gln  Pro  Asp  Ser  Gly  Pro  Pro  Ala  Ala
               60                      65                          70

GCC  CCC  GGC  CAT  CCC  CTG  GCC  CCC  GGC  CCT  CAC  CCG  GCG  GCG  CCC  TCC    291
```

|  |  |  |  |  |  |  |  |  |  |  |  |  |  |  |  |
|---|---|---|---|---|---|---|---|---|---|---|---|---|---|---|---|
| Ala | Pro | Gly | His | Pro | Leu | Ala | Pro | Gly | Pro | His | Pro | Ala | Ala | Pro | Ser |
| 75 |  |  |  |  | 80 |  |  |  |  | 85 |  |  |  |  | 90 |

```
TCC  TGG  GGG  CCC  AGG  CCC  CGC  CGC  TAC  ACG  GTG  CTG  AGC  GTG  GGT  CCC      339
Ser  Trp  Gly  Pro  Arg  Pro  Arg  Arg  Tyr  Thr  Val  Leu  Ser  Val  Gly  Pro
                    95                       100                      105

GGA  GGC  CTG  CGC  AGC  GGG  AGG  CTG  CCC  CTG  CAG  CCC  CGC  GTC  CAG  CTG      387
Gly  Gly  Leu  Arg  Ser  Gly  Arg  Leu  Pro  Leu  Gln  Pro  Arg  Val  Gln  Leu
               110                      115                      120

GAT  GAG  CGC  GGC  CGG  CAG  CGC  GGG  GAC  TTC  TCG  CTA  TGG  CTG  CGC  CCA      435
Asp  Glu  Arg  Gly  Arg  Gln  Arg  Gly  Asp  Phe  Ser  Leu  Trp  Leu  Arg  Pro
          125                      130                      135

GCC  CGG  CGC  GCG  GAC  GCC  GGC  GAG  TAC  CGC  GCC  GCG  GTG  CAC  CTC  AGG      483
Ala  Arg  Arg  Ala  Asp  Ala  Gly  Glu  Tyr  Arg  Ala  Ala  Val  His  Leu  Arg
     140                      145                      150

GAC  CGC  GCC  CTC  TCC  TGC  CGC  CTC  CGT  CTG  CGC  CTG  GGC  CAG  GCC  TCG      531
Asp  Arg  Ala  Leu  Ser  Cys  Arg  Leu  Arg  Leu  Arg  Leu  Gly  Gln  Ala  Ser
155                 160                      165                      170

ATG  ACT  GCC  AGC  CCC  CCA  GGA  TCT  CTC  AGA  GCC  TCC  GAC  TGG  GTC  ATT      579
Met  Thr  Ala  Ser  Pro  Pro  Gly  Ser  Leu  Arg  Ala  Ser  Asp  Trp  Val  Ile
                    175                      180                      185

TTG  AAC  TGC  TCC  TTC  AGC  CGC  CCT  GAC  CGC  CCA  GCC  TCT  GTG  CAT  TGG      627
Leu  Asn  Cys  Ser  Phe  Ser  Arg  Pro  Asp  Arg  Pro  Ala  Ser  Val  His  Trp
               190                      195                      200

TTC  CGG  AAC  CGG  GGC  CAG  GGC  CGA  GTC  CCT  GTC  CGG  GAG  TCC  CCC  CAT      675
Phe  Arg  Asn  Arg  Gly  Gln  Gly  Arg  Val  Pro  Val  Arg  Glu  Ser  Pro  His
          205                      210                      215

CAC  CAC  TTA  GCG  GAA  AGC  TTC  CTC  TTC  CTG  CCC  CAA  GTC  AGC  CCC  ATG      723
His  His  Leu  Ala  Glu  Ser  Phe  Leu  Phe  Leu  Pro  Gln  Val  Ser  Pro  Met
     220                      225                      230

GAC  TCT  GGG  CCC  TGG  GGC  TGC  ATC  CTC  ACC  TAC  AGA  GAT  GGC  TTC  AAC      771
Asp  Ser  Gly  Pro  Trp  Gly  Cys  Ile  Leu  Thr  Tyr  Arg  Asp  Gly  Phe  Asn
235                 240                      245                      250

GTC  TCC  ATC  ATG  TAT  AAC  CTC  ACT  GTT  CTG  GGT  CTG  GAG  CCC  CCA  ACT      819
Val  Ser  Ile  Met  Tyr  Asn  Leu  Thr  Val  Leu  Gly  Leu  Glu  Pro  Pro  Thr
                    255                      260                      265

CCC  TTG  ACA  GTG  TAC  GCT  GGA  GCA  GGT  TCC  AGG  GTG  GGG  CTG  CCC  TGC      867
Pro  Leu  Thr  Val  Tyr  Ala  Gly  Ala  Gly  Ser  Arg  Val  Gly  Leu  Pro  Cys
               270                      275                      280

CGC  CTG  CCT  GCT  GGT  GTG  GGG  ACC  CGG  TCT  TTC  CTC  ACT  GCC  AAG  TGG      915
Arg  Leu  Pro  Ala  Gly  Val  Gly  Thr  Arg  Ser  Phe  Leu  Thr  Ala  Lys  Trp
          285                      290                      295

ACT  CCT  CCT  GGG  GGA  GGC  CCT  GAC  CTC  CTG  GTG  ACT  GGA  GAC  AAT  GGC      963
Thr  Pro  Pro  Gly  Gly  Gly  Pro  Asp  Leu  Leu  Val  Thr  Gly  Asp  Asn  Gly
     300                      305                      310

GAC  TTT  ACC  CTT  CGA  CTA  GAG  GAT  GTG  AGC  CAG  GCC  CAG  GCT  GGG  ACC     1011
Asp  Phe  Thr  Leu  Arg  Leu  Glu  Asp  Val  Ser  Gln  Ala  Gln  Ala  Gly  Thr
315                 320                      325                      330

TAC  ACC  TGC  CAT  ATC  CAT  CTG  CAG  GAA  CAG  CAG  CTC  AAT  GCC  ACT  GTC     1059
Tyr  Thr  Cys  His  Ile  His  Leu  Gln  Glu  Gln  Gln  Leu  Asn  Ala  Thr  Val
                    335                      340                      345

ACA  TTG  GCA  ATC  ATC  ACA  GTG  ACT  CCC  AAA  TCC  TTT  GGG  TCA  CCT  GGA     1107
Thr  Leu  Ala  Ile  Ile  Thr  Val  Thr  Pro  Lys  Ser  Phe  Gly  Ser  Pro  Gly
               350                      355                      360

TCC  TTT  CCT  GGG  ACC  CGG  CAA  GAA  CCA  AAA  ACT  CAC  TCT  CTT  CAA  GGA     1155
Ser  Phe  Pro  Gly  Thr  Arg  Gln  Glu  Pro  Lys  Thr  His  Ser  Leu  Gln  Gly
          365                      370                      375

AAT  CCG  TAA                                                                      1164
Asn  Pro
     380
```

(2) INFORMATION FOR SEQ ID NO:6:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Trp  Glu  Ala  Gln  Phe  Leu  Gly  Leu  Leu  Phe  Leu  Gln  Pro  Leu  Trp
 1                        5                       10                       15

Val  Ala  Pro  Val  Lys  Pro  Leu  Gln  Pro  Gly  Ala  Glu  Val  Pro  Val  Val
                   20                       25                       30

Trp  Ala  Gln  Glu  Gly  Ala  Pro  Ala  Gln  Leu  Pro  Cys  Ser  Pro  Thr  Ile
               35                       40                       45

Pro  Leu  Gln  Asp  Leu  Ser  Leu  Leu  Arg  Arg  Ala  Gly  Val  Thr  Trp  Gln
          50                       55                       60

His  Gln  Pro  Asp  Ser  Gly  Pro  Pro  Ala  Ala  Ala  Pro  Gly  His  Pro  Leu
 65                       70                       75                       80

Ala  Pro  Gly  Pro  His  Pro  Ala  Ala  Pro  Ser  Ser  Trp  Gly  Pro  Arg  Pro
                        85                       90                       95

Arg  Arg  Tyr  Thr  Val  Leu  Ser  Val  Gly  Pro  Gly  Gly  Leu  Arg  Ser  Gly
                   100                      105                      110

Arg  Leu  Pro  Leu  Gln  Pro  Arg  Val  Gln  Leu  Asp  Glu  Arg  Gly  Arg  Gln
               115                      120                      125

Arg  Gly  Asp  Phe  Ser  Leu  Trp  Leu  Arg  Pro  Ala  Arg  Arg  Ala  Asp  Ala
          130                      135                      140

Gly  Glu  Tyr  Arg  Ala  Ala  Val  His  Leu  Arg  Asp  Arg  Ala  Leu  Ser  Cys
145                      150                      155                      160

Arg  Leu  Arg  Leu  Arg  Leu  Gly  Gln  Ala  Ser  Met  Thr  Ala  Ser  Pro  Pro
                   165                      170                      175

Gly  Ser  Leu  Arg  Ala  Ser  Asp  Trp  Val  Ile  Leu  Asn  Cys  Ser  Phe  Ser
               180                      185                      190

Arg  Pro  Asp  Arg  Pro  Ala  Ser  Val  His  Trp  Phe  Arg  Asn  Arg  Gly  Gln
          195                      200                      205

Gly  Arg  Val  Pro  Val  Arg  Glu  Ser  Pro  His  His  His  Leu  Ala  Glu  Ser
210                      215                      220

Phe  Leu  Phe  Leu  Pro  Gln  Val  Ser  Pro  Met  Asp  Ser  Gly  Pro  Trp  Gly
225                      230                      235                      240

Cys  Ile  Leu  Thr  Tyr  Arg  Asp  Gly  Phe  Asn  Val  Ser  Ile  Met  Tyr  Asn
                   245                      250                      255

Leu  Thr  Val  Leu  Gly  Leu  Glu  Pro  Pro  Thr  Pro  Leu  Thr  Val  Tyr  Ala
               260                      265                      270

Gly  Ala  Gly  Ser  Arg  Val  Gly  Leu  Pro  Cys  Arg  Leu  Pro  Ala  Gly  Val
          275                      280                      285

Gly  Thr  Arg  Ser  Phe  Leu  Thr  Ala  Lys  Trp  Thr  Pro  Pro  Gly  Gly  Gly
          290                      295                      300

Pro  Asp  Leu  Leu  Val  Thr  Gly  Asp  Asn  Gly  Asp  Phe  Thr  Leu  Arg  Leu
305                      310                      315                      320

Glu  Asp  Val  Ser  Gln  Ala  Gln  Ala  Gly  Thr  Tyr  Thr  Cys  His  Ile  His
                   325                      330                      335

Leu  Gln  Glu  Gln  Gln  Leu  Asn  Ala  Thr  Val  Thr  Leu  Ala  Ile  Ile  Thr
               340                      345                      350

Val  Thr  Pro  Lys  Ser  Phe  Gly  Ser  Pro  Gly  Ser  Phe  Pro  Gly  Thr  Arg
          355                      360                      365
```

Gln Glu Pro Lys Thr His Ser Leu Gln Gly Asn Pro
370                     375                 380

(2) INFORMATION FOR SEQ ID NO:7:

(i) SEQUENCE CHARACTERISTICS:
        (A) LENGTH: 470 amino acids
        (B) TYPE: amino acid
        (D) TOPOLOGY: linear (xi) SEQUENCE DESCRIPTION: SEQ ID NO:7:

```
                                                Val Pro Val Val
                                                 1
Trp Ala Gln Glu Gly Ala Pro Ala Gln Leu Pro Cys Ser Pro Thr Ile
 5                   10                  15                   20
Pro Leu Gln Asp Leu Ser Leu Leu Arg Arg Ala Gly Val Thr Trp Gln
                 25                  30                  35
His Gln Pro Asp Ser Gly Pro Pro Ala Ala Ala Pro Gly His Pro Leu
             40                  45                  50
Ala Pro Gly Pro His Pro Ala Ala Pro Ser Ser Trp Gly Pro Arg Pro
         55                  60                  65
Arg Arg Tyr Thr Val Leu Ser Val Gly Pro Gly Gly Leu Arg Ser Gly
     70                  75                  80
Arg Leu Pro Leu Gln Pro Arg Val Gln Leu Asp Glu Arg Gly Arg Gln
 85                  90                  95                  100
Arg Gly Asp Phe Ser Leu Trp Leu Arg Pro Ala Arg Arg Ala Asp Ala
                 105                 110                 115
Gly Glu Tyr Arg Ala Ala Val His Leu Arg Asp Arg Ala Leu Ser Cys
             120                 125                 130
Arg Leu Arg Leu Arg Leu Gly Gln Ala Ser Met Thr Ala Ser Pro Pro
         135                 140                 145
Gly Ser Leu Arg Ala Ser Asp Trp Val Ile Leu Asn Cys Ser Phe Ser
     150                 155                 160
Arg Pro Asp Arg Pro Ala Ser Val His Trp Phe Arg Asn Arg Gly Gln
 165                 170                 175                 180
Gly Arg Val Pro Val Arg Glu Ser Pro His His Leu Ala Glu Ser
                 185                 190                 195
Phe Leu Phe Leu Pro Gln Val Ser Pro Met Asp Ser Gly Pro Trp Gly
             200                 205                 210
Cys Ile Leu Thr Tyr Arg Asp Gly Phe Asn Val Ser Ile Met Tyr Asn
         215                 220                 225
Leu Thr Val Leu Gly Leu Glu Pro Pro Thr Pro Leu Thr Val Tyr Ala
     230                 235                 240
Gly Ala Gly Ser Arg Val Gly Leu Pro Cys Arg Leu Pro Ala Gly Val
 245                 250                 255                 260
Gly Thr Arg Ser Phe Leu Thr Ala Lys Trp Thr Pro Pro Gly Gly Gly
                 265                 270                 275
Pro Asp Leu Leu Val Thr Gly Asp Asn Gly Asp Phe Thr Leu Arg Leu
             280                 285                 290
Glu Asp Val Ser Gln Ala Gln Ala Gly Thr Tyr Thr Cys His Ile His
         295                 300                 305
Leu Gln Glu Gln Gln Leu Asn Ala Thr Val Thr Leu Ala Ile Ile Thr
     310                 315                 320
Val Thr Pro Lys Ser Phe Gly Ser Pro Gly Ser Leu Gly Lys Leu Leu
 325                 330                 335                 340
Cys Glu Val Thr Pro Val Ser Gly Gln Glu Arg Phe Val Trp Ser Ser
```

|   |   |   | 345 |   |   |   |   | 350 |   |   |   |   | 355 |   |
|---|---|---|---|---|---|---|---|---|---|---|---|---|---|---|
| Leu | Asp | Thr | Pro | Ser | Gln | Arg | Ser | Phe | Ser | Gly | Pro | Trp | Leu | Glu | Ala |
|   |   |   | 360 |   |   |   |   | 365 |   |   |   |   | 370 |   |
| Gln | Glu | Ala | Gln | Leu | Leu | Ser | Gln | Pro | Trp | Gln | Cys | Gln | Leu | Tyr | Gln |
|   |   |   | 375 |   |   |   |   | 380 |   |   |   |   | 385 |   |
| Gly | Glu | Arg | Leu | Leu | Gly | Ala | Ala | Val | Tyr | Phe | Thr | Glu | Leu | Ser | Ser |
| 390 |   |   |   |   | 395 |   |   |   |   |   | 400 |   |   |   |
| Pro | Gly | Ala | Gln | Arg | Ser | Gly | Arg | Ala | Pro | Gly | Ala | Leu | Pro | Ala | Gly |
| 405 |   |   |   |   | 410 |   |   |   |   | 415 |   |   |   |   | 420 |
| His | Leu | Leu | Leu | Phe | Leu | Thr | Leu | Gly | Val | Leu | Ser | Leu | Leu | Leu | Leu |
|   |   |   |   | 425 |   |   |   |   | 430 |   |   |   |   | 435 |   |
| Val | Thr | Gly | Ala | Phe | Gly | Phe | His | Leu | Trp | Arg | Arg | Gln | Trp | Arg | Pro |
|   |   |   | 440 |   |   |   |   | 445 |   |   |   |   | 450 |   |   |
| Arg | Arg | Phe | Ser | Ala | Leu | Glu | Gln | Gly | Ile | His | Pro | Arg | Leu | Arg |
|   |   |   | 455 |   |   |   |   | 460 |   |   |   |   | 465 |   |
| Ala | Arg |
|   | 470 |

(2) INFORMATION FOR SEQ ID NO:8:

(i) SEQUENCE CHARACTERISTICS:
(A) LENGTH: 457 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:8:

| Met | Cys | Arg | Gly | Phe | Ser | Phe | Arg | His | Leu | Leu | Pro | Leu | Leu | Leu | Leu |
|---|---|---|---|---|---|---|---|---|---|---|---|---|---|---|---|
| 1 |   |   |   | 5 |   |   |   |   | 10 |   |   |   |   | 15 |   |
| Gln | Leu | Ser | Lys | Leu | Leu | Val | Val | Thr | Gln | Gly | Lys | Thr | Val | Val | Leu |
|   |   |   | 20 |   |   |   |   | 25 |   |   |   |   | 30 |   |   |
| Gly | Lys | Glu | Gly | Gly | Ser | Ala | Glu | Leu | Pro | Cys | Glu | Ser | Thr | Ser | Arg |
|   |   | 35 |   |   |   |   | 40 |   |   |   |   | 45 |   |   |   |
| Arg | Ser | Ala | Ser | Phe | Ala | Trp | Lys | Ser | Ser | Asp | Gln | Lys | Thr | Ile | Leu |
|   | 50 |   |   |   |   | 55 |   |   |   |   | 60 |   |   |   |   |
| Gly | Tyr | Lys | Asn | Lys | Leu | Leu | Ile | Lys | Gly | Ser | Leu | Glu | Leu | Tyr | Ser |
| 65 |   |   |   |   | 70 |   |   |   |   | 75 |   |   |   |   | 80 |
| Arg | Phe | Asp | Ser | Arg | Lys | Asn | Ala | Trp | Glu | Arg | Gly | Ser | Phe | Pro | Leu |
|   |   |   |   | 85 |   |   |   |   | 90 |   |   |   |   | 95 |   |
| Ile | Ile | Asn | Lys | Leu | Arg | Met | Glu | Asp | Ser | Gln | Thr | Tyr | Val | Cys | Glu |
|   |   |   | 100 |   |   |   |   | 105 |   |   |   |   | 110 |   |   |
| Leu | Glu | Asn | Lys | Lys | Glu | Glu | Val | Glu | Leu | Trp | Val | Phe | Arg | Val | Thr |
|   |   |   | 115 |   |   |   |   | 120 |   |   |   |   | 125 |   |   |
| Phe | Asn | Pro | Gly | Thr | Arg | Leu | Leu | Gln | Gly | Gln | Ser | Leu | Thr | Leu | Ile |
|   |   |   | 130 |   |   |   |   | 135 |   |   |   |   | 140 |   |   |
| Leu | Asp | Ser | Asn | Pro | Lys | Val | Ser | Asp | Pro | Pro | Ile | Glu | Cys | Lys | His |
| 145 |   |   |   |   | 150 |   |   |   |   | 155 |   |   |   |   | 160 |
| Lys | Ser | Ser | Asn | Ile | Val | Lys | Asp | Ser | Lys | Ala | Phe | Ser | Thr | His | Ser |
|   |   |   |   | 165 |   |   |   |   | 170 |   |   |   |   | 175 |   |
| Leu | Arg | Ile | Gln | Asp | Ser | Gly | Ile | Trp | Asn | Cys | Thr | Val | Thr | Leu | Asn |
|   |   |   | 180 |   |   |   |   | 185 |   |   |   |   | 190 |   |   |
| Gln | Lys | Lys | His | Ser | Phe | Asp | Met | Lys | Leu | Ser | Val | Leu | Gly | Phe | Ala |
|   |   |   | 195 |   |   |   |   | 200 |   |   |   |   | 205 |   |   |
| Ser | Thr | Ser | Ile | Thr | Ala | Tyr | Lys | Ser | Glu | Gly | Glu | Ser | Ala | Glu | Phe |
|   |   |   | 210 |   |   |   |   | 215 |   |   |   |   | 220 |   |   |

```
Ser  Phe  Pro  Leu  Asn  Leu  Gly  Glu  Glu  Ser  Leu  Gln  Gly  Glu  Leu  Arg
225                      230                     235                          240

Trp  Lys  Ala  Glu  Lys  Ala  Pro  Ser  Ser  Gln  Ser  Trp  Ile  Thr  Phe  Ser
                    245                     250                          255

Leu  Lys  Asn  Gln  Lys  Val  Ser  Val  Gln  Lys  Ser  Thr  Ser  Asn  Pro  Lys
               260                     265                          270

Phe  Gln  Leu  Ser  Glu  Thr  Leu  Pro  Leu  Thr  Leu  Gln  Ile  Pro  Gln  Val
          275                     280                     285

Ser  Leu  Gln  Phe  Ala  Gly  Ser  Gly  Asn  Leu  Thr  Leu  Thr  Leu  Asp  Arg
     290                     295                     300

Gly  Ile  Leu  Tyr  Gln  Glu  Val  Asn  Leu  Val  Val  Met  Lys  Val  Thr  Gln
305                 310                     315                          320

Pro  Asp  Ser  Asn  Thr  Leu  Thr  Cys  Glu  Val  Met  Gly  Pro  Thr  Ser  Pro
               325                     330                          335

Lys  Met  Arg  Leu  Ile  Leu  Lys  Gln  Glu  Asn  Gln  Glu  Ala  Arg  Val  Ser
               340                     345                     350

Arg  Gln  Glu  Lys  Val  Ile  Gln  Val  Gln  Ala  Pro  Glu  Ala  Gly  Val  Trp
          355                     360                     365

Gln  Cys  Leu  Leu  Ser  Glu  Gly  Glu  Glu  Val  Lys  Met  Asp  Ser  Lys  Ile
     370                     375                     380

Gln  Val  Leu  Ser  Lys  Gly  Leu  Asn  Gln  Thr  Met  Phe  Leu  Ala  Val  Val
385                     390                     395                          400

Leu  Gly  Ser  Ala  Phe  Ser  Phe  Leu  Val  Phe  Thr  Gly  Leu  Cys  Ile  Leu
                    405                     410                          415

Phe  Cys  Val  Arg  Cys  Arg  His  Gln  Gln  Arg  Gln  Ala  Ala  Arg  Met  Ser
               420                     425                     430

Gln  Ile  Lys  Arg  Leu  Leu  Ser  Glu  Lys  Lys  Thr  Cys  Gln  Cys  Ser  His
               435                     440                     445

Arg  Met  Gln  Lys  Ser  His  Asn  Leu  Ile
     450                     455
```

( 2 ) INFORMATION FOR SEQ ID NO:9:

( i ) SEQUENCE CHARACTERISTICS:
        ( A ) LENGTH: 498 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met  Trp  Glu  Ala  Gln  Phe  Leu  Gly  Leu  Leu  Phe  Leu  Gln  Pro  Leu  Trp
1                        5                          10                       15

Val  Ala  Pro  Val  Lys  Pro  Leu  Gln  Pro  Gly  Ala  Glu  Val  Pro  Val  Val
               20                      25                      30

Trp  Ala  Gln  Glu  Gly  Ala  Pro  Ala  Gln  Leu  Pro  Cys  Ser  Pro  Thr  Ile
          35                      40                      45

Pro  Leu  Gln  Asp  Leu  Ser  Leu  Leu  Arg  Arg  Ala  Gly  Val  Thr  Trp  Gln
     50                      55                      60

His  Gln  Pro  Asp  Ser  Gly  Pro  Pro  Ala  Ala  Ala  Pro  Gly  His  Pro  Leu
65                      70                      75                           80

Ala  Pro  Gly  Pro  His  Pro  Ala  Ala  Pro  Ser  Ser  Trp  Gly  Pro  Arg  Pro
                    85                      90                           95

Arg  Arg  Tyr  Thr  Val  Leu  Ser  Val  Gly  Pro  Gly  Gly  Leu  Arg  Ser  Gly
               100                     105                     110
```

```
Arg Leu Pro Leu Gln Pro Arg Val Gln Leu Asp Glu Arg Gly Arg Gln
        115             120             125

Arg Gly Asp Phe Ser Leu Trp Leu Arg Pro Ala Arg Ala Asp Ala
        130             135             140

Gly Glu Tyr Arg Ala Ala Val His Leu Arg Asp Arg Ala Leu Ser Cys
145             150             155                     160

Arg Leu Arg Leu Arg Leu Gly Gln Ala Ser Met Thr Ala Ser Pro Pro
                165             170             175

Gly Ser Leu Arg Ala Ser Asp Trp Val Ile Leu Asn Cys Ser Phe Ser
                180             185             190

Arg Pro Asp Arg Pro Ala Ser Val His Trp Phe Arg Asn Arg Gly Gln
        195             200             205

Gly Arg Val Pro Val Arg Glu Ser Pro His His Leu Ala Glu Ser
        210             215             220

Phe Leu Phe Leu Pro Gln Val Ser Pro Met Asp Ser Gly Pro Trp Gly
225             230             235                     240

Cys Ile Leu Thr Tyr Arg Asp Gly Phe Asn Val Ser Ile Met Tyr Asn
                245             250             255

Leu Thr Val Leu Gly Leu Glu Pro Pro Thr Pro Leu Thr Val Tyr Ala
                260             265             270

Gly Ala Gly Ser Arg Val Gly Leu Pro Cys Arg Leu Pro Ala Gly Val
        275             280             285

Gly Thr Arg Ser Phe Leu Thr Ala Lys Trp Thr Pro Pro Gly Gly Gly
        290             295             300

Pro Asp Leu Leu Val Thr Gly Asp Asn Gly Asp Phe Thr Leu Arg Leu
305             310             315                     320

Glu Asp Val Ser Gln Ala Gln Ala Gly Thr Tyr Thr Cys His Ile His
                325             330             335

Leu Gln Glu Gln Gln Leu Asn Ala Thr Val Thr Leu Ala Ile Ile Thr
                340             345             350

Val Thr Pro Lys Ser Phe Gly Ser Pro Gly Ser Leu Gly Lys Leu Leu
        355             360             365

Cys Glu Val Thr Pro Val Ser Gly Gln Glu Arg Phe Val Trp Ser Ser
        370             375             380

Leu Asp Thr Arg Ser Gln Arg Ser Phe Ser Gly Pro Trp Leu Glu Ala
385             390             395                     400

Gln Glu Ala Gln Leu Leu Ser Gln Pro Trp Gln Cys Gln Leu Tyr Gln
                405             410             415

Gly Glu Arg Leu Leu Gly Ala Ala Val Tyr Phe Thr Glu Leu Ser Ser
                420             425             430

Pro Gly Ala Gln Arg Ser Gly Arg Ala Pro Gly Ala Leu Pro Ala Gly
        435             440             445

His Leu Leu Leu Phe Leu Thr Leu Gly Val Leu Ser Leu Leu Leu Leu
        450             455             460

Val Thr Gly Ala Phe Gly Phe His Leu Trp Arg Arg Gln Trp Arg Pro
465             470             475                     480

Arg Arg Phe Ser Ala Leu Glu Gln Gly Ile His Pro Arg Arg Leu Arg
                485             490             495

Ala Arg
```

( 2 ) INFORMATION FOR SEQ ID NO:10:

( i ) SEQUENCE CHARACTERISTICS:
        ( A ) LENGTH: 4 amino acids
        ( B ) TYPE: amino acid (C) STRANDEDNESS: single
(D) TOPOLOGY: linear ( i i ) MOLECULE TYPE: peptide ( x i ) SEQUENCE DESCRIPTION: SEQ ID NO:10:

Asp Gly Tyr Cys
1